United States Patent
Filas et al.

(10) Patent No.: US 11,325,876 B2
(45) Date of Patent: *May 10, 2022

(54) PROCESS FOR PRODUCING A CHLORINATED $C_{3-6}$ ALKANE

(71) Applicant: SPOLCHEMIE ZEBRA, A.S., Usti nad Labem (CZ)

(72) Inventors: Karel Filas, Usti nad Labem (CZ); Pavel Kubicek, Decin (CZ); Zdenek Ondrus, Vrbice (CZ); Petr Sladek, Usti nad Labem-Strekov (CZ)

(73) Assignee: SPOLCHEMIE ZEBRA, A.S., Usti nad Labem (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/174,219

(22) Filed: Feb. 11, 2021

(65) Prior Publication Data

US 2021/0188742 A1    Jun. 24, 2021

Related U.S. Application Data

(60) Continuation of application No. 16/375,187, filed on Apr. 4, 2019, now Pat. No. 10,934,232, which is a
(Continued)

(30) Foreign Application Priority Data

Oct. 16, 2014 (CZ) ................................ CZ2014-707

(51) Int. Cl.
   *C07C 17/272* (2006.01)
   *C07C 17/275* (2006.01)
   (Continued)

(52) U.S. Cl.
   CPC ............ *C07C 17/02* (2013.01); *C07C 17/272* (2013.01); *C07C 17/275* (2013.01);
   (Continued)

(58) Field of Classification Search
   None
   See application file for complete search history.

(56) References Cited

U.S. PATENT DOCUMENTS

| | | | |
|---|---|---|---|
| 5,902,914 | A | 5/1999 | Rygas et al. |
| 6,187,978 | B1 | 2/2001 | Rygas et al. |

(Continued)

FOREIGN PATENT DOCUMENTS

| | | |
|---|---|---|
| EP | 131561 | 10/1986 |
| JP | 2013-189402 | 9/2013 |
| WO | WO 2012/053656 | 4/2012 |

*Primary Examiner* — Medhanit W Bahta
(74) *Attorney, Agent, or Firm* — Mark S. Cohen; Pearl Cohen Zedek Latzer Baratz

(57) ABSTRACT

Disclosed is a process for producing a chlorinated C3-6 alkane comprising providing a reaction mixture comprising an alkene and carbon tetrachloride in a principal alkylation zone to produce chlorinated C3-6 alkane in the reaction mixture, and extracting a portion of the reaction mixture from the principal alkylation zone, wherein:

a) the concentration of the chlorinated C3-6 alkane in the reaction mixture in the principal alkylation zone is maintained at a level such that the molar ratio of chlorinated C3-6 alkane:carbon tetrachloride in the reaction mixture extracted from the alkylation zone does not exceed 95:5 when the principal alkylation zone is in continuous operation; and/or b) the reaction mixture extracted from the principal alkylation zone additionally comprises alkene and the reaction mixture is subjected to a dealkenation step in which at least about 50% or more by weight of the alkene present in the reaction mixture is extracted therefrom and at least about 50% of the extracted alkene is fed back into the reaction mixture provided in the principal alkylation zone; and/or c) the reaction mixture present in the principal alkylation zone and extracted from the principal alkylation zone
(Continued)

additionally comprises a catalyst, and the reaction mixture extracted from the principal alkylation zone is subjected to an aqueous treatment step in which the reaction mixture is contacted with an aqueous medium in an aqueous treatment zone, a biphasic mixture is formed and an organic phase comprising catalyst is extracted from the biphasic mixture.

7 Claims, 4 Drawing Sheets

Related U.S. Application Data division of application No. 15/858,234, filed on Dec. 29, 2017, now Pat. No. 10,294,179, which is a continuation of application No. 14/882,492, filed on Oct. 14, 2015, now Pat. No. 9,896,400.

(51) Int. Cl.
*C07C 17/278* (2006.01)
*C07C 17/38* (2006.01)
*C07C 19/01* (2006.01)
*C07C 17/02* (2006.01)
*C07C 17/383* (2006.01)

(52) U.S. Cl.
CPC ............ *C07C 17/278* (2013.01); *C07C 17/38* (2013.01); *C07C 17/383* (2013.01); *C07C 19/01* (2013.01); *Y02P 20/582* (2015.11)

(56) References Cited

U.S. PATENT DOCUMENTS

| | | |
|---|---|---|
| 6,313,360 B1 | 11/2001 | Wilson et al. |
| 6,452,057 B1 * | 9/2002 | Lambert .................. B01J 23/72 570/162 |
| 6,552,238 B1 | 4/2003 | Mainz et al. |
| 6,720,466 B2 | 4/2004 | Wilson et al. |
| 7,102,041 B2 | 9/2006 | Tung et al. |
| 8,115,038 B2 | 2/2012 | Wilson et al. |
| 8,633,340 B2 | 1/2014 | Smith et al. |
| 2008/0091053 A1 | 4/2008 | Tung et al. |
| 2012/0035402 A1 | 2/2012 | Wilson et al. |
| 2013/0165705 A1 | 6/2013 | Hosaka et al. |
| 2014/0171698 A1 | 6/2014 | Elsheikh et al. |
| 2014/0221705 A1 | 8/2014 | Wang et al. |
| 2014/0228601 A1 | 8/2014 | Dawkins et al. |
| 2014/0235907 A1 | 8/2014 | Yang et al. |
| 2014/0275659 A1 | 9/2014 | Yang et al. |
| 2015/0197467 A1 | 7/2015 | Pigamo et al. |
| 2018/0148394 A1 | 5/2018 | Pigamo et al. |

* cited by examiner

PROCESS FOR PRODUCING A CHLORINATED $C_{3-6}$ ALKANE

CROSS-REFERENCE TO RELATED APPLICATIONS

This application is a continuation of U.S. application Ser. No. 16/375,187, filed Apr. 4, 2019, which is a divisional of U.S. application Ser. No. 15/858,234, filed Dec. 29, 2017, now U.S. Pat. No. 10,294,179, issued May 21, 2019, which is a continuation of U.S. application Ser. No. 14/882,492, filed Oct. 14, 2015, now U.S. Pat. No. 9,896,400, issued Feb. 20, 2018, which claims priority of Czech Patent Application No. PV 2014-707, filed Oct. 16, 2014, all of which are hereby incorporated by reference.

The present invention relates to processes for producing high purity chlorinated $C_{3-6}$ alkane compounds, such as tetrachloropropane, pentachloropropane, pentachlorobutane, and heptachlorohexane, and also to compositions comprising such compounds.

Haloalkanes find utility in a range of applications. For example, halocarbons are used extensively as refrigerants, blowing agents and foaming agents. Throughout the second half of the twentieth century, the use of chlorofluoroalkanes increased exponentially until the 1980's, when concerns were raised about their environmental impact, specifically regarding depletion of the ozone layer.

Subsequently, fluorinated hydrocarbons such as perfluorocarbons and hydrofluorocarbons have been used in place of chlorofluoroalkanes, although more recently, environmental concerns about the use of that class of compounds have been raised and legislation has been enacted in the EU and elsewhere to reduce their use.

New classes of environmentally friendly halocarbons are emerging and have been investigated, and in some cases, embraced in a number of applications, especially as refrigerants in the automotive and domestic fields. Examples of such compounds include 1,1,1,2-tetrafluoroethane (R-134a), 2-chloro-3,3,3-trifluoropropene (HFO-1233xf), 1,3,3,3-tetrafluoropropene (HFO-1234ze), 3,3,3-trifluoropropene (HFO-1243zf), and 2,3,3,3-tetrafluoropropene (HFO-1234yf), 1,2,3,3,3-pentafluoropropene (HFO-1225ye), 1-chloro-3,3,3-trifluoropropene (HFO-1233zd), 3,3,4,4,4-pentafluorobutene (HFO-1345zf), 1,1,1,4,4,4-hexafluorobutene (HFO-1336mzz), 3,3,4,4,5,5,5-heptafluoropentene (HFO1447fz), 2,4,4,4-tetrafluorobut-1-ene (HFO-1354mfy) and 1,1,1,4,4,5,5,5-octafluoropentene (HFO-1438mzz).

While these compounds are, relatively speaking, chemically non-complex, their synthesis on an industrial scale to the required levels of purity is challenging. Many synthetic routes proposed for such compounds increasingly use, as starting materials or intermediates, chlorinated alkanes or alkenes. Historically, many of the processes developed for the production of such compounds involved the addition of chlorinated alkanes to fluorinated olefins. However, such processes were found not to be acceptably efficient and to result in the production of numerous impurities. More recently developed processes are typically more direct and involve the conversion of the chlorinated alkane or alkene starting materials or feedstock, to the fluorinated target compounds using hydrogen fluoride and transition metal catalysts, for example chromium-based catalysts.

It has been recognised that when the chlorinated feedstock is obtained from a multi-step process, especially if such steps are linked and run continuously to achieve industrially acceptable product volumes, then the need to prevent cumulative side reactions from generating unacceptable impurities at each process step is very important.

The purity of the chlorinated starting materials will have a substantial effect on the success and viability of the processes (especially continuous processes) for preparing the desirable fluorinated products. The presence of certain impurities will result in side reactions, minimising the yield of the target compound. Removal of these impurities even using intensive distillation steps is also challenging. Additionally, the presence of certain impurities will compromise catalyst life, by, for example, by poisoning the catalyst.

Accordingly, there is a need for efficient, reliable and highly selective processes for preparing high purity chlorinated alkanes for use in the synthesis of the fluorinated compounds mentioned above, as well as other specialty compounds. Several processes for producing purified chlorinated compounds have been proposed in the art, for example U.S. Pat. Nos. 6,187,978, 6,313,360, US2008/091053, U.S. Pat. Nos. 6,552,238, 6,720,466, JP2013-189402 and US2014/0171698.

Despite these advances, problems can still arise through the use of chlorinated compounds obtained from the processes discussed above. Particularly, the presence of impurities especially those which are not easily separable from the compounds of interest (e.g. as a result of similar boiling points) or which reduce the effectiveness or operating life of catalysts used in downstream processes can be problematic.

To minimise such drawbacks, a demand remains for high purity chlorinated alkane compounds, and also for efficient, reliable and highly selective processes for preparing such compounds.

Thus according to one aspect of the present invention, there is provided a process for producing a chlorinated $C_{3-6}$ alkane comprising providing a reaction mixture comprising an alkene and carbon tetrachloride in a principal alkylation zone to produce the chlorinated $C_{3-6}$ alkane in the reaction mixture, and extracting a portion of the reaction mixture from the principal alkylation zone, wherein:

a) the concentration of the chlorinated $C_{3-6}$ alkane in the reaction mixture in the principal alkylation zone is maintained at a level such that the molar ratio of chlorinated $C_{3-6}$ alkane:carbon tetrachloride in the reaction mixture extracted from the principal alkylation zone does not exceed:

95:5 where the principal alkylation zone is in continuous operation, or

99:1 where the principal alkylation zone is in batchwise operation; and/or b) the reaction mixture extracted from the principal alkylation zone additionally comprises alkene and the reaction mixture is subjected to a dealkenation step in which at least about 50% or more by weight of the alkene present in the reaction mixture is extracted therefrom and at least about 50% of the extracted alkene is fed back into the reaction mixture provided in the principal alkylation zone, and/or c) the reaction mixture present in the principal alkylation zone and extracted from the principal alkylation zone additionally comprises a catalyst, and the reaction mixture extracted from the principal alkylation zone is subjected to an aqueous treatment step in which the reaction mixture is contacted with an aqueous medium in an aqueous treatment zone, a biphasic mixture is formed, and an organic phase comprising catalyst is extracted from the biphasic mixture.

The processes of the present invention are centred around a highly selective telomerisation reaction which takes place partially or completely in the principal alkylation zone. In that reaction, carbon tetrachloride is reacted with an alkene to produce a $C_{3-6}$ chlorinated alkane. While telomerisation reactions to produce $C_{3-6}$ chlorinated alkanes are known in the art, one issue with such processes is the production of unwanted impurities; a need remains for a process for producing high purity $C_{3-6}$ chlorinated alkanes, in industrial volumes and ideally on a continuous basis.

It has unexpectedly and advantageously been found that conducting one, some or all of steps a) to c) as outlined above when preparing chlorinated $C_{3-6}$ alkane from alkene and carbon tetrachloride improves efficiency (including reducing energy consumption) and/or minimises the formation of impurities which may otherwise be difficult to remove from the chlorinated $C_{3-6}$ alkane of interest and/or be problematic in downstream reactions in which the chlorinated $C_{3-6}$ alkane may be employed. Further, surprisingly, the processes of the present invention balance these advantages with high selectivity and high yield.

The reaction mixture is formed by contacting the alkene and carbon tetrachloride. This may occur in the principal alkylation zone, e.g. by both the alkene and carbon tetrachloride being fed into that zone. Additionally or alternatively, the alkene may be contacted with carbon tetrachloride in a zone upstream of the principal alkylation zone and then fed into the principal alkylation zone.

In embodiments of the invention, the molar ratio of chlorinated $C_{3-6}$ alkane:carbon tetrachloride in the reaction mixture is controlled within certain numerically defined limits. As those skilled in the art will appreciate, in such embodiments, while control over the process is characterised herein in terms of the molar ratio between the carbon tetrachloride starting material and the $C_{3-6}$ chlorinated alkane product, it can also considered as control over the conversion of starting material to product—thus a molar ratio of starting material:product of 95:5 equates to a conversion of 5%. The inventors have found that limiting the conversion of the starting material as outlined above minimises the formation of undesirable impurities. Additionally, where reference is made to a molar ratio of the starting material:product being greater than a given value, this means a greater degree of conversion of the starting material to product, i.e. such that the proportion of the product is increased while the proportion of the starting material is decreased.

For example, in embodiments of the invention, a primary alkylation zone may be employed, upstream of the principal alkylation zone. The reaction mixture may be formed by feeding carbon tetrachloride and the alkene into the primary alkylation zone to form the reaction mixture which is then fed into the principal alkylation zone. In such an embodiment, the partial conversion of carbon tetrachloride to the $C_{3-6}$ chlorinated alkane of interest may occur in the primary alkylation zone such that that alkane is formed and comprised in the reaction mixture fed into the principal alkylation zone, along with carbon tetrachloride. In additional or alternative embodiments, the amount of alkene fed into the primary alkylation zone may be limited to retard the conversion of carbon tetrachloride to the $C_{3-6}$ chlorinated alkane of interest in the primary alkylation zone such that the reaction mixture fed into the principal alkylation zone therefrom comprises carbon tetrachloride and the $C_{3-6}$ chlorinated alkane, but low levels or substantially no alkene.

The alkene and carbon tetrachloride employed in the processes of the present invention may be contacted in a zone (for example, a primary alkylation zone or the principal alkylation zone) by being fed into that zone using any technique or equipment known to those skilled in the art, for example via dispersion devices such as dip tube/s, nozzle/s, ejectors, static mixing devices and/or sparger/s. In such embodiments, the feed of alkene and/or carbon tetrachloride may be continuous or intermittent. The alkene supplied as a feed into the zone in which the reaction mixture is formed may be in liquid and/or gaseous form. Likewise, the carbon tetrachloride may be in liquid and/or gaseous form.

In embodiments of the present invention, the reaction mixture (comprising carbon tetrachloride, the $C_{3-6}$ chlorinated alkane product and optionally catalyst and/or unreacted alkene) present in the principal alkylation zone (and/or any other alkylation zone that may be employed) may be homogenous, i.e. in a single phase, for example a liquid, or gaseous phase. This can be achieved even where one of the components of the reaction mixture is introduced into the system in a different phase to the other components. For example, in embodiments, gaseous alkene may be contacted with liquid carbon tetrachloride, causing the alkene to be dissolved, thus forming a liquid phase homogenous reaction mixture. Alternatively, the reaction mixture may be heterogeneous.

Thus according to one aspect of the present invention, there is provided a process for producing a chlorinated $C_{3-6}$ alkane comprising providing a reaction mixture comprising an alkene and carbon tetrachloride in a primary alkylation zone to produce chlorinated $C_{3-6}$ alkane in the reaction mixture, and extracting a portion of the reaction mixture from the primary alkylation zone and feeding the extracted portion of the reaction mixture into a principal reaction zone and extracting a portion of the reaction mixture from the principal reaction zone, wherein the molar ratio of chlorinated $C_{3-6}$ alkane:carbon tetrachloride in the reaction mixture extracted from the principal alkylation zone is higher than the molar ratio of chlorinated $C_{3-6}$ alkane:carbon tetrachloride in the reaction mixture extracted from the primary alkylation zone.

The alkene used in the processes of the present invention may be a $C_{2-5}$ alkene, for example, an ethene (i.e. a $C_2$ alkene), a propene, a butene or a pentene. The alkene may or may not be halogenated, e.g. chlorinated and/or substituted. In arrangements in which the alkene is chlorinated, it preferably comprises 1, 2, 3, 4 or 5 chlorine atoms. In embodiments of the present invention, the chloroalkene has the general formula: $CH_aX_b=R$, where a is 1 or 2, b is 0 or 1, X is halogen (e.g. chlorine) and R is substituted or unsubstituted $C_{1-4}$ alkyl.

Examples of alkene materials that may be employed in the processes of the present invention include ethene, vinyl chloride, propene, 2-chloropropene, 3-chloropropene, 2,3,3,3-Tetrachloropropene, 1,1-dichloroethene, trichloroethene, chlorofluoroethene, 1,2-dichloroethene, 1,1-dichloro-difluoroethene, 1-chloropropene, 1-chlorobutene and/or any of the other alkenes disclosed in U.S. Pat. No. 5,902,914 and EP131561, the contents of which are incorporated by reference.

The carbon tetrachloride and alkene starting materials employed in the processes of the present invention may have a high degree of purity, for example, either or both of those materials may be at least about 95% pure, at least about 97% pure, at least about 99% pure, at least about 99.5% pure, at least about 99.7% pure, or at least about 99.9% pure.

In embodiments of the present invention, the carbon tetrachloride starting material comprises less than less than about 2000 ppm, less than about 1000 ppm, less than about 500 ppm, less than about 200 ppm, less than about 100 ppm, less than about 50 ppm or less than about 20 ppm bromides or brominated organic compounds.

Additionally or alternatively, the carbon tetrachloride starting material may have a moisture content of about 200 ppm or less, about 100 ppm or less, about 50 ppm or less or about 35 ppm or less.

In the processes of the present invention, the carbon tetrachloride is preferably employed as the haloalkane feedstock. However, in alternative embodiments of the present invention, haloalkane feedstocks other than carbon tetrachloride may be employed, for example 1,1-dichloromethane, 1,1,1-trichloroethane, dichlorofluoromethane, 1,1,1-trichlorotrifluoroethane, 1,1,2-trichlorotrifluoroethane, tetrachloroethane, pentachloroethane, hexachloroethane and/or any of the other chloroalkanes disclosed in U.S. Pat. No. 5,902,914, the contents of which are incorporated herein.

The source of carbon tetrachloride may be located on the same site as the apparatus for operating the processes of the present invention. In embodiments, the source of the carbon tetrachloride may be adjacent to a chlor alkali facility with, for example, a membrane electrolysis plant, from which high purity chlorine will be available to use in the production of the carbon tetrachloride. The site may also comprise plants for producing epichlorohydrin (for example from glycerol feedstock), glycidol, and/or epoxy resin, such that hydrogen chloride gas, produced as a byproduct in any associated steps or processes, is effectively also utilised. Thus for best economic use of a chlor alkali facility, an integrated facility with plants for chlorine reactions and capture/re-use of hydrogen chloride is envisioned.

The reaction mixture may be extracted from the principal alkylation zone (and/or, if employed, the primary alkylation zone) on a continuous or intermittent basis. For the avoidance of doubt, where reference is made in the present application to the continuous extraction of material from the zones employed in the process of the present invention, this should not be assigned a purely literal meaning. One skilled in the art would recognise that, in such embodiments, material may be removed on a substantially continuous basis while the zone in question is at operating conditions and, if its purpose is to set up a steady state reaction (e.g. an alkylation), once the reaction mixture therein has attained the required steady state.

One of the advantages of the present invention is that the presence of certain impurities typically observed in commercially supplied alkene (such as certain organic impurities, e.g. as alcohols, ethers, esters, and aldehydes) can be tolerated and/or removed using process steps outlined herein. This advantage is especially beneficial in arrangements in which the alkene is ethene; the ethene may be derived from bioethanol, from ethanol or from crude oil.

An additional advantage of the processes of the present invention is that i) the continuous production of chlorinated alkane and ii) substantially full utilisation of the alkene starting material can be achieved with no escape of the alkene into the off-gas system.

The chlorinated $C_{3-6}$ alkane may be a chloropropane, a chlorobutane, a chloropentane or a chlorohexane. The chlorinated $C_{3-6}$ alkane may comprise 4, 5, 6, 7, 8 or more chlorine atoms. Examples of chlorinated $C_{3-6}$ alkane compounds which may be produced in high purity according to the processes of the present invention include tetrachloropropane, e.g. 1,1,1,3-tetrachloropropane, tetrachlorobutane, hexachlorobutane, heptachlorobutane, octachlorobutane pentachloropropane, pentachlorobutane, e.g. 1,1,1,3,3-pentachlorobutane, and heptachlorohexane.

One of the advantages of the processes of the present invention is that they may permit the production of a target $C_{3-6}$ chlorinated alkane with high isomeric selectivity. Thus, in such embodiments of the invention, the $C_{3-6}$ chlorinated alkane product is produced with isomeric selectivity of at least about 95%, at least about 97%, at least about 98%, at least about 99%, at least about 99.5%, at least about 99.7%, at least about 99.8% or at least about 99.9%

The alkylation reaction conducted in the process of the present invention, to produce chlorinated $C_{3-6}$ alkane may be accelerated through the use of a catalyst. As used herein, the term catalyst is used to encompass not only the use of a single compound or material having catalytic effect, e.g. a solid metal or a metal salt, but a catalyst system which may additionally comprise a catalytic material and a co-catalyst or promoter such as a ligand.

Any catalyst known by those skilled in the art to find utility in the formation of a chlorinated $C_{3-6}$ alkane from carbon tetrachloride and alkene may be employed.

In embodiments of the invention, the catalyst is metallic. Any metal which can function as a catalyst in the alkylation reaction of the present invention may be employed, including, but not limited to copper and/or iron. The metallic catalyst may be present in its solid form (e.g., in the case of copper or iron, in particulate form (e.g. powder or filings), wire and/or mesh or the like) and/or as a salt in which the metal may be in any oxidation state (e.g. cuprous salts such as cuprous chloride, cuprous bromide, cuprous cyanide, cuprous sulphate, cuprous phenyl and/or ferrous and/or ferric salts such as ferrous chloride and ferric chloride).

Where metallic salts are employed as catalysts in the processes of the present invention, these may be added to the alkylation zone/s and/or form in situ therein. In the latter case, solid metal may be added into the alkylation zone/s and, owing to the conditions therein, the salt may be formed. For example, if solid iron is added into a chlorination reaction mixture, the chlorine present may combine with the elemental iron to form ferric or ferrous chloride in situ. Where metallic salts are formed in situ, it may nevertheless be desirable to maintain a predetermined level of elemental metal catalyst in the reaction mixture (for example, an excess of elemental metal as compared to the level of metallic salt/s and/or ligand) and thus, additional elemental metal catalyst may be added as the reaction proceeds, either continuously or intermittently.

As mentioned above, in embodiments of the present invention, the catalyst may also comprise a ligand, preferably an organic ligand, which may form a complex with the metallic catalyst. Suitable ligands include amines, nitrites, amides, phosphates and phosphites. In embodiments of the invention, the ligand employed is an alkylphosphate, such as trimethylphosphate, triethylphosphate, tributylphosphate, and triphenylphosphate.

Additional metallic catalysts and ligands are known to those skilled in the art and are disclosed in the prior art, for example, U.S. Pat. No. 6,187,978, the contents of which are incorporated by reference.

The components of the catalyst system, where used, may be fed into the alkylation zone/s (e.g. the principal alkylation zone, and/or, if used, the primary alkylation zone) continuously or intermittently. Additionally or alternatively, they may be introduced into the alkylation zone/s (e.g. the principal alkylation zone, and/or, if used, the primary alkylation zone) prior to and/or during commencement of the alkylation reaction.

Additionally or alternatively, the catalyst (or components of the catalyst, for example the ligand) may be fed into the alkylation zone/s (e.g. the principal alkylation zone, or, if used, the primary alkylation zone) together with other components of the reaction mixture, for example in a feed of carbon tetrachloride and/or ethene.

In embodiments of the invention in which the catalyst comprises a metallic catalyst and a promoter such as a ligand, the molar ratio of the promoter:metallic catalyst in the reaction mixture present in the principal alkylation zone, and/or, if used, the primary alkylation zone is maintained at a ratio of greater than 1:1, more preferably at a ratio of greater than 2:1, 5:1 or 10:1.

Where solid metal catalyst is added to the reaction mixture, this may be added into the primary alkylation zone, if used, and/or into the principal alkylation zone. In embodiments of the invention, solid metal catalyst is added into the primary alkylation zone, if used, and/or into the principal alkylation zone in amounts to maintain a level of about 0.1 to 4%, about 0.5 to 3% or about 1 to 2% by weight of the reaction mixture.

Additionally or alternatively, where metallic catalysts are employed, these are added to establish a dissolved metal content of about 0.1%, about 0.15% or about 0.2% to about 1.0, about 0.5 or about 0.3% by weight of the reaction mixture.

In embodiments of the invention in which the catalyst system employed comprises a metallic catalyst and promoter, the metallic catalyst and promoter can be added to the reaction mixture simultaneously and/or in the same part of the apparatus, for example in the primary alkylation zone (if used) and or the principal alkylation zone.

Alternatively, the metallic catalyst and promoter can be added at different locations in the apparatus, or sequentially or separately. For example, solid metal catalyst can be added to the primary alkylation zone with promoter being fed into that zone from a recycle loop to which additional, fresh promoter may also be added.

In embodiments of the invention, the primary and/or principal alkylation zones are operated under atmospheric or superatmospheric pressure, i.e. at a pressure greater than about 100 kPa, greater than about 200 kPa, greater than about 300 kPa, greater than about 400 kPa, greater than about 500 kPa, greater than about 600 kPa, greater than about 700 kPa, or greater than about 800 kPa. Typically, the pressure in the primary and/or principal alkylation zones will be equal to or lower than about 2000 kPa, about 1700 kPa, about 1500 kPa, about 1300 kPa, about 1200 kPa or about 1000 kPa.

Additionally or alternatively, in embodiments of the invention, the primary and/or principal alkylation zones are operated at elevated temperatures, i.e. temperatures equal to or greater than about 30° C., about 40° C., about 50° C., about 60° C., about 70° C., about 80° C., about 90° C. or about 100° C. Typically, the primary and/or principal alkylation zones will be operated at temperatures equal to or lower than about 200° C., about 180° C., about 160° C., about 140° C., about 130° C., about 120° C., or about 115° C.

The use of temperatures and pressures within these ranges combined with the other features of the processes of the present invention have been advantageously found to maximise yields and/or selectivity of the chlorinated $C_{3-6}$ alkane of interest, while minimising the formation of problematic byproducts.

In processes of the invention, a plurality of alkylation zones may be employed. Any number of alkylation zones may be employed, for example 1, 2, 3, 4, 5, 6, 7, 8, 9 or 10 or more. In embodiments in which a plurality of primary and/or principal alkylation zones are employed, there may be any number (for example 1, 2, 3, 4, 5, 6, 7, 8, 9, or 10 or more) primary and/or principal alkylation zones present.

For the avoidance of doubt, where reference is made to the properties of an alkylation zone (primary and/or principal), e.g. its operating conditions, its method of operation, its properties, etc., insofar as embodiments of the present invention are concerned which comprise a plurality of primary and/or principal alkylation zones, one, some or all of those zones may exhibit the property/ies in question. For example, if, for brevity, reference is made to a principal alkylation zone having a specified operating temperature, then, insofar as embodiments including a plurality of principal alkylation zones are concerned, this should be taken as a reference that one, some or all of those principal alkylation zones are operated at the specified temperature.

In arrangements where a plurality of primary and/or principal alkylation zones are employed, those alkylation zones may be operated in parallel and/or in series.

In arrangements in which primary and principal alkylation zones are employed, the alkylation reaction between alkene and carbon tetrachloride may be controlled to prevent it proceeding beyond a certain degree of completion in the primary alkylation zone, for example such that the molar ratio of chlorinated $C_{3-6}$ alkane:carbon tetrachloride in the reaction mixture extracted from the primary alkylation zone and/or fed into the principal alkylation zone does not exceed 85:15, 90:10, 93:7 or 95:5 although this is not essential. Additionally or alternatively, the reaction may be permitted to run to a relatively advanced stage of completion, such that the molar ratio of chlorinated $C_{3-6}$ alkane:carbon tetrachloride in the reaction mixture extracted from the primary alkylation zone and/or fed into the principal alkylation zone is greater than 50:50, 60:40, 70:30, 75:25 or 80:20.

Control of the progress of the alkylation reaction in the primary alkylation zone may be achieved through the use of reaction conditions which do not favour the total conversion of carbon tetrachloride to 1,1,1,3-Tetrachloropropane. Additionally, or alternatively, control of the progress of the alkylation reaction in the primary alkylation zones may be achieved through careful selection of the residence time of the reaction mixture in the primary alkylation zones, for example about 20 to 300 minutes, about 40 to 250 minutes, about 60 to about 200 minutes or about 90 to about 180 minutes. In embodiments of the invention, the molar ratio may be controlled by limiting the amount of alkene fed into the primary and/or principal alkylation zones. For example, the molar ratio of carbon tetrachloride:alkene fed into the primary and/or principal alkylation zones may range from about 50:50 to about 55:45, about 60:40, about 65:35, about 70:30, about 75:25, about 80:20 about 85:15 or about 90:10.

In embodiments where primary and principal alkylation zones are employed, the bulk of chlorinated $C_{3-6}$ alkane may be produced in the primary alkylation zone. In such embodiments, the proportion of the $C_{3-6}$ alkane produced in the principal reaction zone may be significantly lower e.g. such that the molar ratio of chlorinated $C_{3-6}$ alkane:carbon tetrachloride in the reaction mixture is increased by 1 to 10, 2 to 8 or 3 to 5.

For example, if the molar ratio of chlorinated $C_{3-6}$ alkane: carbon tetrachloride in the reaction mixture extracted from the primary alkylation zone and fed into the principal alkylation zone is 90:10, that molar ratio may be increased by 2, 3 or 5 in the principal alkylation zone so that the molar ratio of chlorinated $C_{3-6}$ alkane:carbon tetrachloride present in the mixture extracted from the principal alkylation zone may be 92:8, 93:7 or 95:5.

However, the viability of the processes of the present invention is not dependent on the major part of the conversion of carbon tetrachloride to the chlorinated $C_{3-6}$ alkane of interest occurring in the primary reaction zone. Thus, in alternative embodiments, the degree of conversion of carbon tetrachloride to the chlorinated $C_{3-6}$ alkane of interest may be balanced between the primary and principal alkylation zones, or may be greater in the principal alkylation zone than in the primary alkylation zone.

The reaction mixture may then be taken from the primary alkylation zone (continuously or intermittently) and fed into the principal alkylation zone in which a proportion of the remaining carbon tetrachloride present in the reaction mixture is converted to the chlorinated $C_{3-6}$ alkane of interest. In such embodiments, any unreacted alkene starting material present in the reaction mixture may advantageously be fully (or at least nearly fully) utilised.

In processes of the invention, where employed, the primary and principal alkylation zones may be operated under different conditions. The principal alkylation zone may be operated under a greater pressure than the primary alkylation zone/s, for example at a pressure which is at least about 10 kPa higher, about 20 kPa higher, about 50 kPa higher, about 100 kPa higher, about 150 kPa higher, about 200 kPa higher, about 300 kPa or about 500 kPa higher.

In embodiments of the invention, alkene may not be fed into the principal alkylation zone; the only source of alkene to those zone/s may be in the reaction mixture fed into the principal alkylation zone.

Additionally, in embodiments in which the alkylation reaction between carbon tetrachloride and alkene is catalysed by a metallic catalyst (optionally including a ligand), metallic catalyst and/or ligand may not be fed in to the principal alkylation zone. In such embodiments, the sole source of catalyst may be the reaction mixture fed into the principal alkylation zone. Additionally or alternatively, the principal alkylation zone may be provided with a catalyst bed.

In processes of the present invention in which primary and principal alkylation zones are employed and solid metal catalyst is present in the reaction mixture in the primary alkylation zone (e.g. by being added directly thereto), when the reaction mixture is extracted from the primary alkylation zone in order to be fed into the principal alkylation zone, the extraction of the reaction mixture from the primary alkylation zone may be carried out such that very little, if any, solid metal catalyst is present in the reaction mixture, for example less than about 5 mg, about 2 mg, about 1 mg, about 0.5 mg, about 0.2 mg, about 0.1 mg of solid metal catalyst per litre of reaction mixture.

This may be achieved through the use of any technique and/or equipment known to those skilled in the art, for example a tube extending into the primary alkylation zone/s at an appropriate location, being provided with a filtering mesh and/or having an appropriate diameter.

Where employed, the primary and principal alkylation zones may be in the same or different reactors, which may be the same or different types of reactors. Further, in embodiments where a plurality of primary alkylation zones are employed, these may be in the same or different reactors. Likewise, in embodiments where a plurality of principal alkylation zones are employed, these may be in the same or different reactors.

Any type of reactor or reactors known to those skilled in the art may be employed in the processes of the present invention. Specific examples of reactors that may be used to provide alkylation zones are column reactors (e.g. column gas-liquid reactors), tubular reactors, bubble column reactions, plug/flow reactors (e.g. tubular plug/flow reactors) and stirred tank reactors (e.g. continuously stirred tank reactors).

Arrangements in which the primary alkylation zone is present in a continuously stirred tank reactor (CSTR) and the principal alkylation zone is present in a plug/flow reactor have provided advantageous results.

One advantage of the process of the present invention is that desirous results are obtained whether the alkylation zones (e.g. the primary alkylation zone and/or the principal alkylation zone) are operated in a continuous (steady state) or batchwise process. The terms 'continuous process' and 'batchwise process' will be understood by those skilled in the art.

In embodiments, the primary alkylation zone, where employed, is operated in a continuous or batchwise process. Additionally or alternatively, the second alkylation zone/s, where employed, are operated in a continuous or batchwise process.

In processes of the present invention, the concentration of the chlorinated $C_{3-6}$ alkane in the reaction mixture in the principal alkylation zone is maintained at a level such that the molar ratio of chlorinated $C_{3-6}$ alkane:carbon tetrachloride in the reaction mixture extracted from the principal alkylation zone does not exceed: i) 95:5, where the principal alkylation zone is in continuous operation, or ii) 99:1 where the principal alkylation zone is in batchwise operation.

In certain embodiments of the invention where the principal alkylation zone is in continuous operation, the content of the chlorinated $C_{3-6}$ alkane may be controlled such that the ratio of that compound:carbon tetrachloride in the reaction mixture extracted from the principal alkylation zone does not exceed about 94:6, about 92:8, or about 90:10

In alternative embodiments of the invention where the principal alkylation zone is in batchwise operation, the content of the chlorinated $C_{3-6}$ alkane may be controlled such that the ratio of that compound:carbon tetrachloride in the reaction mixture extracted from the principal alkylation zone does not exceed about 97:3, about 95:5, or about 90:10.

Regardless of whether the principal alkylation zone is in continuous or batchwise process, the content of the chlorinated $C_{3-6}$ alkane may be controlled such that the ratio of that compound:carbon tetrachloride in the reaction mixture extracted from the principal alkylation zone is equal to or greater than about 70:30, about 80:20, about 85:15, or about 90:10.

It has surprisingly been found that by controlling the degree of conversion of carbon tetrachloride to the chlorinated $C_{3-6}$ alkane of interest, and preventing the reaction from proceeding to completion, the formation of impurities is advantageously reduced. For example, in embodiments in which the alkene feedstock employed in the processes of the present invention is ethene, the production of undesired byproducts such as pentanes (which would otherwise be formed) is minimized.

Thus, in embodiments of the invention, reaction mixture extracted from the principal reaction zone comprises serial reaction products, i.e. compounds comprising a greater number of carbon atoms than the $C_{3-6}$ chlorinated alkane product, of less than about 5%, less than about 2%, less than about 1%, less than about 0.5%, less than about 0.2%, less than about 0.1%, less than about 0.05% or less than about 0.02%.

Control of the content of the chlorinated $C_{3-6}$ alkane may be achieved by retarding the progress of the alkylation process and/or by introducing additional carbon tetrachloride into the principal alkylation zone.

In embodiments in which the content of the chlorinated $C_{3-6}$ alkane is controlled by retarding the alkylation process, this can be achieved through the use of reaction conditions which do not favour the total conversion of carbon tetrachloride to 1,1,1,3-Tetrachloropropane. For example, this can be achieved through exposing the reaction mixture, or at least a portion thereof, to conditions which decelerate or halt the progress of the alkylation reaction. In such embodiments, the pressure that the reaction mixture is exposed to in the alkylation zone/s (for example, the principal alkylation zone/s, where employed) could be reduced significantly, e.g. by at least about 500 kPA, by at least about 700 kPa, by at least about 1000 kPa.

Additionally or alternatively, the pressure to which the reaction mixture is exposed can be reduced to atmospheric or subatmospheric pressure. The reduction in pressure can occur in one or more alkylation zone (for example, one, some or all of the principal alkylation zones, if used). Additionally or alternatively, the reduction in pressure can occur following extraction of the reaction mixture from the alkylation zone/s.

Additionally or alternatively, in embodiments in which the content of the chlorinated $C_{3-6}$ alkane is controlled by retarding the alkylation process, this can be achieved through limiting the alkene level present in the reaction mixture.

In embodiments of the invention, control of the progress of the alkylation reaction in the alkylation zone/s may be achieved through careful selection of the residence time of the reaction mixture in the alkylation zone/s. For example, in embodiments in which one or more principal alkylation zones are employed, the residence time of the reaction mixture in those zone/s may be, for example about 1 to 120 minutes, about 5 to 100 minutes, about 15 to about 60 minutes or about 20 to about 40 minutes.

In embodiments in which the content of the chlorinated $C_{3-6}$ alkane is controlled by retarding the alkylation process, this can additionally or alternatively be achieved by reducing the operating temperature of the principal alkylation zone, for example by about 5° C. or more, about 10° C. or more, about 20° C. or more, about 50° C. or more or by about 100° C. or more. Additionally or alternatively, the operating temperature of the principal conversion zone can be reduced to about 20° C., about 10° C. or about 0° C.

Additionally or alternatively, the alkylation process can be retarded by limiting the amount of catalyst present in the reaction mixture, or removing the catalyst bed (if present) from the principal alkylation zone.

The rate of agitation or stirring of the principal alkylation zone can also be reduced to retard the alkylation process.

As mentioned above, the reaction mixture extracted from the principal alkylation zone comprises carbon tetrachloride and chlorinated $C_{3-6}$ alkane. However, in embodiments of the invention, depending on the conditions and equipment employed, the reaction mixture extracted from the principal alkylation zone may additionally comprise unreacted alkene starting material, catalyst, and/or impurities (e.g. chlorinated alkane impurities, chlorinated alkene impurities and/or oxygenated organic compounds).

Given that the presence of unreacted alkene alongside the chlorinated $C_{3-6}$ alkane can be problematic, particularly for downstream processes employing the chlorinated $C_{3-6}$ alkane, in embodiments of the invention, the reaction mixture extracted from the principal alkylation zone is subjected to a dealkenation step in which at least about 50% or more by weight of the alkene present in the reaction mixture is extracted therefrom and at least about 50% of the extracted alkene is fed back into the reaction mixture provided in the principal alkylation zone.

Such embodiments are particularly advantageous as they enable substantial if not total utilisation of the alkene feed employed in the processes of the present invention.

In embodiments of the invention, at least about 60%, at least about 70%, at least about 80%, at least about 90%, at least about 95%, at least about 97% or at least about 99% of the alkene present in the reaction mixture extracted from the principal alkylation zone is removed during the dealkenation step.

The removal of unreacted alkene from the reaction mixture can be achieved using any technique known to those skilled in the art. In embodiments of the invention, extraction of the alkene from the reaction mixture can be achieved using distillation techniques which result in a stream rich in alkene being obtained, for example flash evaporation, which may conveniently be deployed in embodiments where the boiling point of the alkene is substantially lower than the boiling point of the other compounds present in the reaction mixture, as is the case with ethene (−103.7° C.) vs carbon tetrachloride (76.6° C.) and 1,1,1,3-Tetrachloropropane (159° C.).

Dealkenation of the reaction mixture may be selective. In other words, the alkene is selectively extracted, without the substantial removal of other compounds from the reaction mixture. In such embodiments, the alkene extracted from the reaction mixture may comprise less than about 10%, less than about 5%, less than about 2% or less than about 1% of compounds other than the alkene starting material.

Distillation of the reaction mixture can be achieved through any techniques or using any equipment known to those skilled in the art. For example, conventional distillation apparatus (e.g. a distillation column) may be employed. Additionally or alternatively, in embodiments of the invention, where pressure in the principal alkylation zone from which the reaction mixture is extracted is superatmospheric, evaporation of alkene from the reaction mixture may be achieved by maintaining the reaction mixture at a superatmospheric pressure following extraction from the principal alkylation zone and feeding it into an evaporation zone in which evaporation of the alkene from the reaction mixture occurs.

In embodiments of the invention, evaporation of alkene from the reaction mixture in the evaporation zone can be achieved by depressurisation, for example, by significantly reducing the pressure that the reaction mixture is under, e.g. by at least about 500 kPA, by at least about 700 kPa, by at least about 1000 kPa, and/or to atmospheric or subatmospheric pressure. Conveniently, in embodiments in which depressurisation is used either partly or totally to decelerate or halt the conversion of carbon tetrachloride to the chlorinated $C_{3-6}$ alkane of interest, and also to separate alkene from the reaction mixture, these aims can be simultaneously achieved in a single depressurisation step.

The evaporation zone may be in any apparatus in which evaporation of the alkene present in the reaction mixture can be achieved, for example, flash evaporation apparatus such as a flash drum.

The alkene distilled off from the reaction mixture, for example by flash evaporation, is preferably extracted from the distillation apparatus in liquid or gaseous form.

In processes of the present invention, at least about 50%, at least about 70%, at least about 80%, at least about 90%, at least about 95%, at least about 97% or at least about 99% by weight of the of the alkene extracted from the evaporation zone is fed back (i.e. recycled) to the primary and/or principal alkylation zone.

For the avoidance of doubt, in embodiments of the invention, the distilled alkene, if in gaseous form, may or may not be converted back to a liquid, prior to being fed in to the reaction mixture provided in the principal alkylation zone. For example, conversion of the gaseous alkene to liquid alkene may be achieved by being passed through a condenser and/or being trapped in a stream of liquid (preferably cooled) carbon tetrachloride, which can then be fed into the alkylation zone/s. Gaseous alkene may be trapped in a liquid stream of carbon tetrachloride using any techniques or equipment known to those skilled in the art, for example an absorption column. This arrangement is advantageous as it aids the full industrial utilisation of the compounds employed in the alkylation process.

As mentioned above, in embodiments of the invention, a catalyst, for example a catalyst system comprising solid metal and/or metallic salt catalyst and a promoter such as a ligand, may be employed in the reaction mixture present in the alkylation zone/s. In such embodiments, reaction mixture extracted from the alkylation zone/s may comprise catalyst. Given that the presence of catalyst may be problematic in downstream reactions employing the chlorinated $C_{3-6}$ alkane, it may be preferable to remove the catalyst from the reaction mixture.

Additionally, for catalyst systems in which costly catalysts and/or promoters such as the alkylphosphate and alkylphosphite ligands mentioned above are employed, the recovery of reusable catalyst systems and/or components thereof is also preferable to minimise the quantities of fresh catalyst that must be used, thus reducing operational cost.

While the challenge of removing catalysts of the type employed in the processes of the present invention from reaction mixtures has been addressed in the past, the techniques and conditions employed to do so (typically involving distillation using aggressive conditions) can be damaging to the catalyst systems and can reduce their catalytic ability.

This is especially the case where the catalyst system is temperature sensitive as is the case for systems including certain organic ligands as promoters, such as alkylphosphates and alkylphosphites.

Thus, in embodiments of the present invention, the reaction mixture extracted from the principal alkylation zone is subjected to an aqueous treatment step in which the reaction mixture is contacted with an aqueous medium in an aqueous treatment zone, a biphasic mixture is formed and an organic phase comprising catalyst is extracted from the biphasic mixture.

In embodiments of the invention in which reaction mixture is subjected to an aqueous treatment step, the reaction mixture may comprise unreacted carbon tetrachloride and $C_{3-6}$ chlorinated alkane product. Additionally, the reaction mixture may comprise catalyst (for example a complex of the metallic catalyst and catalyst ligand, or the free catalyst ligand) and/or unreacted alkene starting material.

Through the use of the aqueous treatment step, the damaging conditions described in the prior art (for example, high temperature, high catalyst concentration and/or the presence of iron compounds in anhydrous form) can be avoided, meaning that the recovered catalyst and/or components thereof (e.g. the ligand or promoter) can be re-used (for example, it can be recycled back to the reaction mixture provided in the alkylation zone/s) without any substantial loss in catalytic ability. In embodiments of the invention, the steam stripping of the biphasic aqueous treated mixture is preferred as the boiler temperatures in excess of 100° C. can be avoided and atmospheric pressure can be employed.

A further advantage of the aqueous treatment step is that it results in the removal of impurities from the reaction mixture, for example, oxygenated organic products, if present. More specifically, when processes involve alkenes as precursors, e.g. ethene, propene, 1-butene, 2-butene, 1-hexene, 3-hexene, 1-phenyl-3-hexene, butadiene, vinyl halides and the like, oxygenated organic compounds (e.g. alkanols, alkanoyls and chlorinated analogues of such oxygenated compounds) may potentially be formed. Advantageously, the levels of such materials in the reaction mixture are significantly reduced to acceptable levels, if not eliminated, by the aqueous treatment step.

In embodiments of the invention in a which an aqueous treatment step is performed, the reaction mixture provided in the aqueous treatment zone may comprise the chlorinated $C_{3-6}$ alkane of interest (for example in amounts of about 50% or greater), catalyst, and optionally carbon tetrachloride and/or impurities, for example organic oxygenated compounds, chlorinated alkane compounds (other than the chlorinated $C_{3-6}$ alkane of interest) and or chlorinated alkene compounds.

This catalytic recovery process involves the reaction mixture being subjected to an aqueous treatment step in which the reaction mixture is contacted with an aqueous medium in an aqueous treatment zone. In embodiments, the aqueous medium is water (as a liquid and/or vapour). Additionally, the aqueous medium may additionally comprise other compounds, such as acids. Inorganic acids, such as hydrochloric acid, sulfuric acid and/or phosphoric acid may be employed.

Where the aqueous medium fed into the aqueous treatment zone is partially or totally in liquid form, a biphasic mixture will be formed upon the liquid aqueous medium contacting the reaction mixture.

Alternatively, where the aqueous medium is in gaseous form, e.g. steam, a biphasic mixture may not be formed immediately, but only once the gaseous aqueous medium condenses. The apparatus employed in aqueous treatment step may be configured such that condensation of the aqueous medium to form the biphasic mixture occurs within and/or remote from the aqueous treatment zone.

In embodiments of the invention, the $C_{3-6}$ chlorinated alkane product may be extracted from the mixture formed in the aqueous treatment zone. The majority (e.g. at least about 50%, at least about 60%, at least about 70%, at least about 80% or at least about 90%) of the chlorinated $C_{3-6}$ alkane present in the reaction mixture fed into the aqueous treatment zone may be extracted from the mixture formed in the aqueous treatment zone using any techniques or equipment known to those skilled in the art.

In embodiments of the invention, distillation is used to extract the $C_{3-6}$ chlorinated alkane product from the mixture formed in the aqueous treatment zone. The distillation may result in a stream rich in $C_{3-6}$ chlorinated alkane product being obtained.

As used throughout this specification, the term 'a stream rich in' a specific compound (or corresponding language) is used to mean that the stream comprises at least about 90%, about 95%, about 97%, about 98% or about 99% of the specific compound. Further, the term 'stream' should not be interpreted narrowly, but encompasses compositions (including fractions) extracted from a mixture via any means.

For example, the $C_{3-6}$ alkane may be distilled off, for example, from a gaseous mixture comprising that alkane and water vapour. The $C_{3-6}$ chlorinated alkane may be distilled off in a stream rich in $C_{3-6}$ chlorinated alkane. In embodiments of the invention in which the aqueous medium is partly or totally in liquid form, distillation of the $C_{3-6}$ chlorinated alkane may be achieved by boiling the mixture present to evaporate the chlorinated $C_{3-6}$ alkane and produce the gaseous chlorinated $C_{3-6}$ alkane/water vapour mixture from which the chlorinated $C_{3-6}$ alkane can be distilled, for example using steam distillation techniques.

Additionally or alternatively, where the aqueous medium is provided partly or totally in gaseous form, this evaporates the chlorinated $C_{3-6}$ alkane to form the gaseous mixture comprising that alkane and water vapour which can then optionally be subjected to distillation to remove the chlorinated $C_{3-6}$ alkane, for example steam distillation. The $C_{3-6}$ chlorinated alkane may be obtained in a stream rich in that compound.

In embodiments in which the chlorinated $C_{3-6}$ alkane is distilled from a gaseous mixture of chlorinated $C_{3-6}$ alkane and water vapour, the distillation apparatus may be coupled to the aqueous treatment zone so that the gaseous chlorinated alkane/water vapour mixture can pass directly from the aqueous treatment zone to that apparatus. Alternatively, the distillation apparatus may be located remotely from the aqueous treatment zone such that the gaseous mixture is firstly extracted from the aqueous treatment zone and then conveyed to the distillation apparatus. In either arrangement, the $C_{3-6}$ chlorinated alkane may be obtained in a stream rich in that compound.

In alternative embodiments, where the aqueous medium and reaction mixture are in liquid form, the chlorinated $C_{3-6}$ alkane may be extracted from that liquid mixture using conventional distillation techniques known to those skilled in the art. The $C_{3-6}$ chlorinated alkane may be obtained in a stream rich in that compound.

The biphasic mixture may be formed within the aqueous treatment zone or remotely therefrom. The biphasic mixture comprises an aqueous phase (as a result of the aqueous medium added to the aqueous treatment zone) and an organic phase (comprising chlorinated $C_{3-6}$ alkane, optionally unreacted carbon tetrachloride, and importantly catalyst).

To maximise the volume of the organic phase and thus facilitate extraction of that phase from the biphasic mixture, a haloalkane extraction agent (e.g. carbon tetrachloride and/or the chlorinated $C_{3-6}$ alkane of interest) may be added to the biphasic mixture (e.g. by being continuously or intermittently fed into the aqueous treatment zone) using techniques and equipment known to those skilled in the art.

The organic phase can be extracted from the biphasic residue using any technique known to those skilled in the art, e.g. decantation. For example, extraction of the organic phase can be performed by the sequential phase extraction from the aqueous treatment zone or the vessel in which it is contained. Alternatively, the biphasic mixture can be extracted from the aqueous treatment zone and subjected to a phase separation step remote from the aqueous treatment zone.

In embodiments of the invention, the biphasic mixture and/or the extracted organic phase can be filtered. In embodiments, this will result in a filter cake being obtained which can optionally be totally or partially employed as a source of iron.

Extraction of the $C_{3-6}$ chlorinated alkane product from the mixture formed during the aqueous treatment step may be performed prior to extraction of the organic phase therefrom, and/or after the organic phase is extracted from that mixture.

Some exemplary embodiments in which the $C_{3-6}$ chlorinated alkane product is extracted from the mixture formed during the aqueous treatment step are outlined above.

As a further example, the biphasic mixture may be heated to form a gaseous mixture from which $C_{3-6}$ chlorinated alkane product can be extracted (optionally as a stream rich in $C_{3-6}$ chlorianted alkane), e.g. via distillation. The organic phase, having a reduced proportion of $C_{3-6}$ chlorinated alkane, may then be extracted from the biphasic mixture.

Additionally or alternatively, the organic phase may be extracted from the biphasic mixture as discussed above. $C_{3-6}$ chlorinated alkane may then be extracted (optionally as a stream rich in $C_{3-6}$ chlorianted alkane) from that phase, e.g. via distillation. In such embodiments, where the organic phase comprises catalyst, the distillation conditions selected to extract the $C_{3-6}$ chlorinated alkene are mild so as to minimise deactivation of the catalyst system, for example at a temperature of about 100° C. or lower, about 95° C. or lower, about 90° C. or lower, about 85° C. or lower or about 80° C. or lower, and/or at a pressure of about 1 to 10 kPa. Lower pressures can additionally or alternatively be used.

The extracted organic phase may comprise carbon tetrachloride and/or $C_{3-6}$ chlorinated alkane product. Additionally, the reaction mixture may comprise catalyst (for example the complex of a metallic catalyst and catalyst ligand or free ligand) and/or unreacted alkene starting material. Once a stream rich in $C_{3-6}$ chlorinated alkane has been extracted from the mixture formed in the aqueous treatment step (either directly, or following extraction of the organic phase therefrom), the content of $C_{3-6}$ chlorinated alkane of that phase will be lower than in the reaction mixture.

In arrangements of the invention, especially those in which the organic phase comprises carbon tetrachloride and/or catalyst, the organic phase may be fed back to the alkylation zone/s, for example in liquid form. In such arrangements, alkene starting material (e.g. in gaseous form) may be trapped in the organic phase stream being fed into the alkylation zone/s.

In embodiments of the invention, one or more distillation steps in addition to those discussed above may be performed at any point in the process, optionally to obtain stream/s rich in specific products. For example, prior to an aqueous treatment step, if performed, the reaction mixture can be subjected to a distillation step. In embodiments in which the reaction mixture contains a temperature sensitive catalyst system, e.g. one including an organic ligand as a promoter, the distillation step is typically conducted under conditions to avoid deactivation of the catalyst, for example at a temperature of about 100° C. or lower, about 95° C. or lower, about 90° C. or lower, about 85° C. or lower or about 80° C. or lower, and/or at a pressure of about 1 to 10 kPa. Lower pressures can additionally or alternatively be used.

Additionally, it has been found that the inactivation of temperature sensitive catalyst systems can be avoided by not over-distilling the reaction mixture. Thus, in embodiments of the invention in which reaction mixture containing a catalyst system is distilled, distillation may not be permitted to result in the volume of the process liquid in the distillation apparatus being reduced such that the concentration of the catalyst system in that process liquid is about 2×, about 5× or about 10× higher than the level of that catalyst system present in the reaction mixture provided in the principal alkylation zone.

A distillation step conducted prior to the aqueous treatment step (if performed) can be carried out using techniques and equipment known to those skilled in the art, for example, a distillation boiler (batch or continuous) in communication with a vacuum distillation column. In such an embodiment, the reaction mixture subjected to distillation may comprise greater than about 50% by weight of the chlorinated $C_{3-6}$ alkane of interest, catalyst, and optionally carbon tetrachloride and/or impurities, for example organic oxygenated compounds, chlorinated alkane compounds (other than the chlorinated $C_{3-6}$ alkane of interest) and or chlorinated alkene compounds.

The distillation step typically results in the removal of chlorinated alkane distillate stream/s, for example stream/s of (and optionally rich in) unreacted carbon tetrachloride, the $C_{3-6}$ alkane of interest, and/or chlorinated organic impurities (i.e. chlorinated organic compounds other than the $C_{3-6}$ alkane of interest and carbon tetrachloride) from the reaction mixture. The carbon tetrachloride may be recycled back to the alkylation zone/s. The residue from such a step, which typically comprises quantities of the chlorinated $C_{3-6}$ alkane, carbon tetrachloride and/or catalyst, may be subjected to further treatment steps, e.g. an aqueous treatment step and/or further distillation step/s.

In embodiments of the invention, where the reaction mixture is subjected to a distillation step prior to the aqueous treatment step (if performed), at least about 30%, at least about 50%, at least about 60% or at least about 70% to at most about 95%, at most about 90%, at most about 85% or at most about 80% by weight of the chlorinated $C_{3-6}$ alkane of interest is removed from the reaction mixture in that distillation step.

One or more distillation steps may additionally or alternatively be performed following the aqueous treatment step (if performed). For example, the chlorinated $C_{3-6}$ alkane extracted from the reaction mixture fed into the aqueous treatment zone may be present in the form of a mixture comprising, as the major constituent, the chlorinated $C_{3-6}$ alkane, a haloalkane extraction agent, as well as chlorinated organic impurities (i.e. chlorinated organic compounds other than the $C_{3-6}$ alkane of interest and carbon tetrachloride). That mixture may be subjected to one or more distillation steps, to remove chlorinated organic impurities, to obtain a stream rich in $C_{3-6}$ chlorinated alkane and/or to remove the haloalkane extraction agent. Again, any equipment or conditions known to those skilled in the art may be employed in such a distillation step, for example a distillation boiler (batch or continuous) in communication with a vacuum distillation column.

In such a distillation step, the chlorinated $C_{3-6}$ alkane extracted from the reaction mixture provided in the aqueous treatment zone may be subjected to distillation to separate the chlorinated $C_{3-6}$ alkane of interest from chloroalkane impurities. For example, in embodiments in which the chlorinated $C_{3-6}$ alkane of interest is 1,1,1,3-Tetrachloropropane, a distillation step to purify the chlorinated $C_{3-6}$ alkane extracted from the reaction mixture provided in the aqueous treatment zone has been found to be particularly effective in removing chloropentane/chloropentene impurities.

Chlorinated organic impurities separated from mixtures comprising the chlorinated $C_{3-6}$ alkane of interest in distillation steps performed at any stage in processes of the present invention may be retrieved and re-used in the production of carbon tetrachloride. This may be achieved by subjecting the chlorinated organic impurities to a high temperature chlorinolysis process. In such a process, any chlorinated organic compounds present are re-processed mainly back to pure tetrachloromethane in high yields. Thus the use of a chlorinolysis step in the processes of the present invention is useful to maximise the overall yield of the synthesis and purity of the target chloroalkane while minimising waste production.

Regardless of the identity of the chlorinated $C_{3-6}$ alkane of interest, in embodiments of the invention, a residue of 'heavies' may be formed in a distillation boiler if used following the aqueous treatment step. The 'heavies' residue is typically extracted from the system and treated, for example, to a high temperature chlorinolysis process preferably leading to the production of chloromethanes.

The processes of the present invention are particularly advantageous as they enable highly pure chlorinated alkanes to be produced. Though using simple and straightforward techniques and equipment with which one skilled in the art would be familiar.

As can be seen from the disclosure provided herein, the inventive processes of the present invention can be operated in an integrated process in a fully continuous mode, optionally in combination with other processes. The process steps of the present invention may employ starting compounds which are converted to highly pure intermediates which are themselves further processed to the required target chlorinated compounds. Those compounds have the requisite purity to be employed as feedstocks in a range of downstream processes, for example hydrofluorination conversions.

The processes of the present invention enable product purity levels to be controlled to attain high purity levels of the compounds at each step. The processes advantageously balance high yields, high selectivity and high efficiency which is particularly challenging, especially in continuous processes. The processes of the present invention enable high purity chloroalkane compounds to be economically produced on an industrial scale, those compounds having very low levels of a range of impurities, such as haloalkanes, or haloalkenes, (particularly those which are isomeric to the compound of interest and/or which have a higher molecular weight, such as the products of serial reactions), and/or oxygenated and/or brominated analogues, as well as water, and metallic species.

In embodiments of the invention, the processes of the invention can be used to produce high purity chlorinated alkane compositions which comprise:

About 99.0% or more, about 99.5% or more, about 99.7% or more, about 99.8% or more or about 99.9% or more of the chlorinated alkane.

less than about 2000 ppm, less than about 1000 ppm, less than about 500 ppm, less than about 200 ppm or less than about 100 ppm chlorinated alkane impurities (i.e. chlorinated alkane compounds other than the chlorinated $C_{3-6}$ alkane of interest), less than about 2000 ppm, less than about 1000 ppm, less than about 500 ppm, less than about 200 ppm or less than about 100 ppm chlorinated alkene compounds, less than about 2000 ppm, less than about 1000 ppm, less than about 500 ppm, less than about 200 ppm or less than about 100 ppm oxygenated organic compounds, less than about 500 ppm, less than about 200 ppm, less than about 100 ppm, less than about 50 ppm or less than about 20 ppm metallic catalyst, less than about 500 ppm, less than about 200 ppm, less than about 100 ppm, less than about 50 ppm or less than about 20 ppm catalyst promoter, less than about 2000 ppm, less than about 1000 ppm, less than about 500 ppm, less than about 200 ppm or less than about 100 ppm bromides or brominated organic compounds, and/or less than about 1000 ppm, less than about 500 ppm, less than about 200 ppm, less than about 100 ppm, less than about 50 ppm or less than about 20 ppm of water.

In embodiments in which the chlorinated $C_{3-6}$ alkane of interest is 1,1,1,3-tetrachloropropane, the following are examples of specific impurities which are minimized, not produced and/or removed in the processes of the present invention: Trichloromethane, 1,2-Dichloroethane, 1-Chlorobutane, 1,1,1-Trichloropropane, Tetrachloroethene, 1,1,3-Trichloroprop-1-ene, 1,1,1,3,3-Pentachloropropane, 1,1,1,2,3-Pentachloropropane, hexachloroethane, 1,1,1,5-Tetrachloropentane, 1,3,3,5-Tetrachloropentane, Tributylphosphate, chlorinated alkanol and chlorinated alkanoyl compounds.

Thus, in embodiments of the present invention, product 1,1,1,3-tetrachloropropane comprises about 500 ppm or less, about 200 ppm or less, about 100 ppm or less, about 50 ppm or less, about 20 ppm or less or about 10 ppm or less of one or more of those compounds.

For the avoidance of doubt, where the purity of a composition or material is presented by percentage or ppm, unless otherwise stated, this is a percentage/ppm by weight.

As mentioned previously, the prior art fails to disclose or teach processes for producing chlorinated alkanes having such a high degree of purity, where a global range of possible impurities are managed. Thus, according to further aspects of the present invention, there are provided high purity chlorinated alkane compositions as set out above.

| 1 | ethene feed stream |
| 2 | particulate iron feed stream |
| 3 | continuously stirred tank reactor |
| 4 | plug/flow reactor |
| 5 | reaction mixture stream |
| 6 | flash evaporation vessel |
| 7 | 1,1,1,3-tetrachloropropane-rich mixture stream |
| 8 | evaporated ethene stream |
| 9 | condenser |
| 10 | ethene stream |
| 11 | absorption column |
| 12 | carbon tetrachloride and tributyl phosphate/ferric chloride catalyst feed stream |
| 13 | stream of recovered catalyst (tributyl phosphate/ferric chloride), fresh catalyst and carbon tetrachloride |
| 14 | cooler |
| 15 | cooled stream of recovered catalyst (tributyl phosphate/ferric chloride), fresh catalyst and carbon tetrachloride |
| 16 | off-gas |

Figure 2:
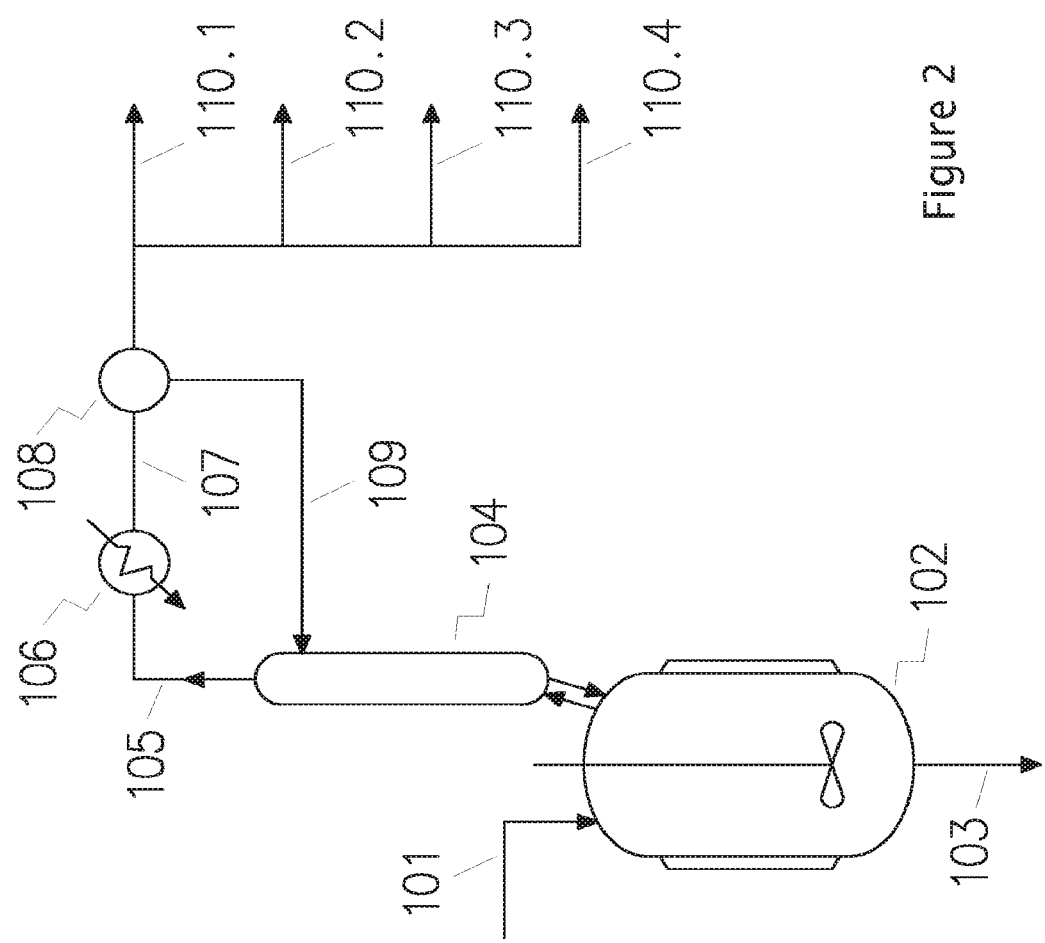

FIG. 2—First distillation step

Figure 1:
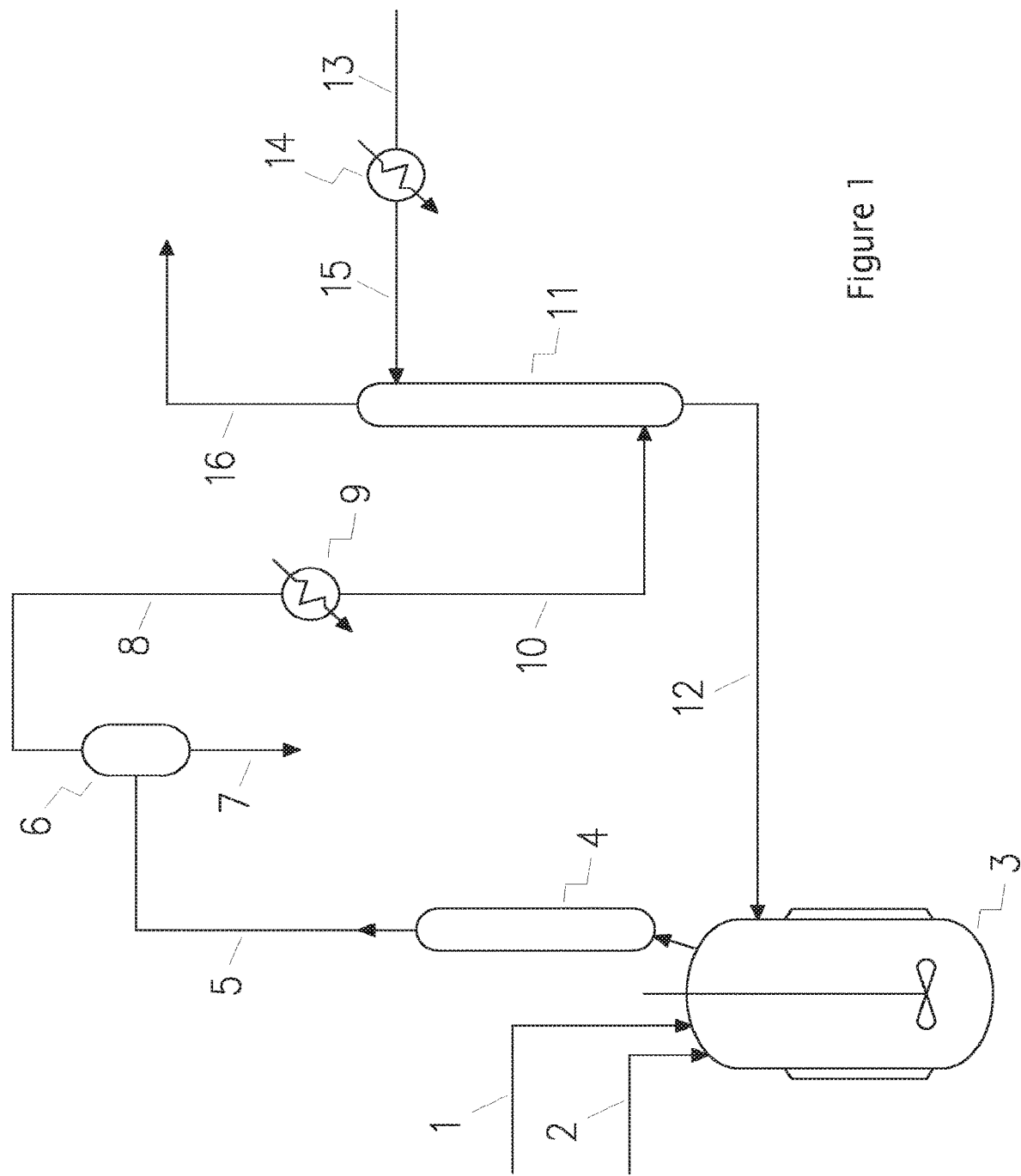
FIG. 1—Alkylation step

| 101 | 1,1,1,3-tetrachloropropane-rich mixture stream extracted from the flash evaporation vessel (6), FIG. 1 |
| 102 | batch distillation boiler |
| 103 | stream of 1,1,1,3-tetrachloropropane-rich mixture comprising catalyst |
| 104 | vacuum distillation column |
| 105 | distillate stream |
| 106 | condenser |
| 107 | intermediate line |
| 108 | reflux divider |
| 109 | reflux stream |
| 110.1 | light ends stream |
| 110.2 | carbon tetrachloride stream |
| 110.3 | tetrachloroethene stream |
| 110.4 | purified 1,1,1,3-tetrachloropropane product stream |

Figure 3:
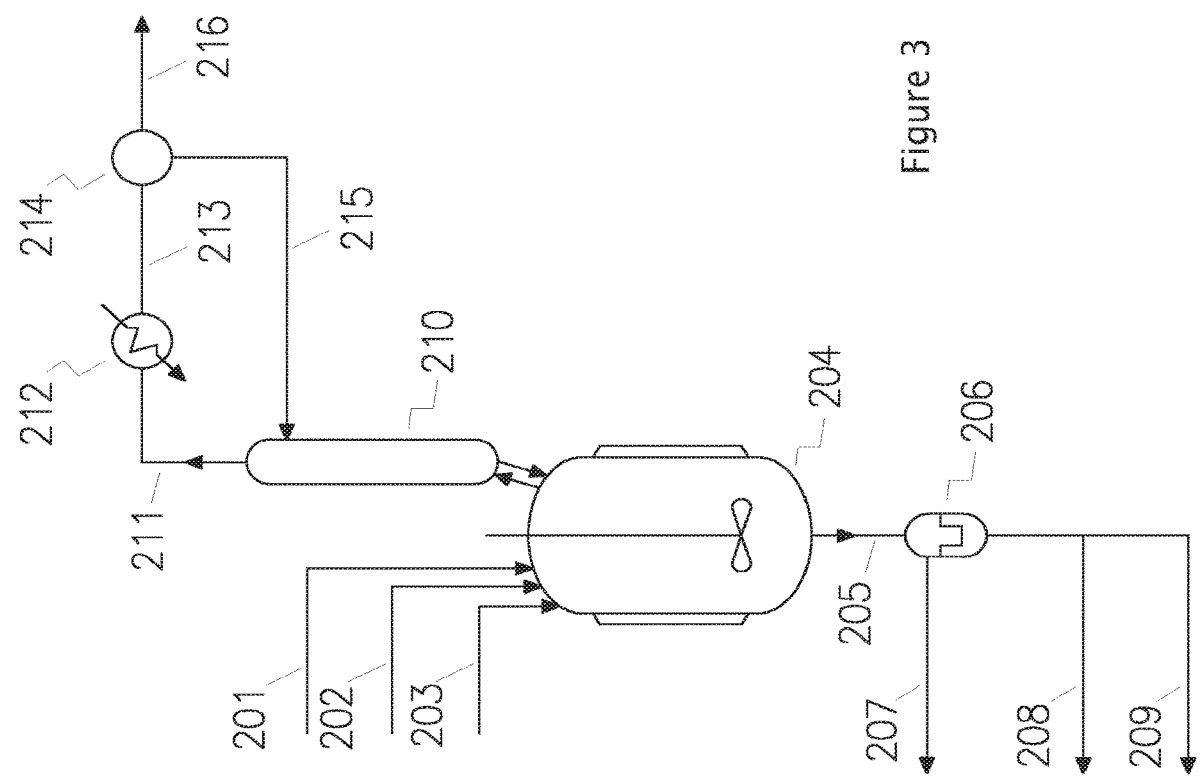

FIG. 3—Aqueous catalyst recovery step

| 201 | weak hydrochloric acid solution stream |
| 202 | 1,1,1,3-tetrachloropropane-rich mixture feed stream comprising catalyst |
| 203 | haloalkane extraction agent feed stream (1,1,1,3-tetrachloropropane) |
| 204 | batch distillation boiler |
| 205 | batch distillation boiler outlet |
| 206 | filtration |
| 207 | filter cake removal |
| 208 | organic phase extraction (part of the feed stream 13 in FIG. 1) |
| 209 | aqueous phase disposal |
| 210 | column for steam distillation of crude 1,1,1,3-tetrachloropropane |
| 211 | crude 1,1,1,3-tetrachloropropane stream |
| 212 | condenser |
| 213 | condensed crude 1,1,1,3-tetrachloropropane stream |
| 214 | reflux liquid-liquid separator |
| 215 | reflux stream |
| 216 | crude 1,1,1,3-tetrachloropropane stream for further distillation |

Figure 4:
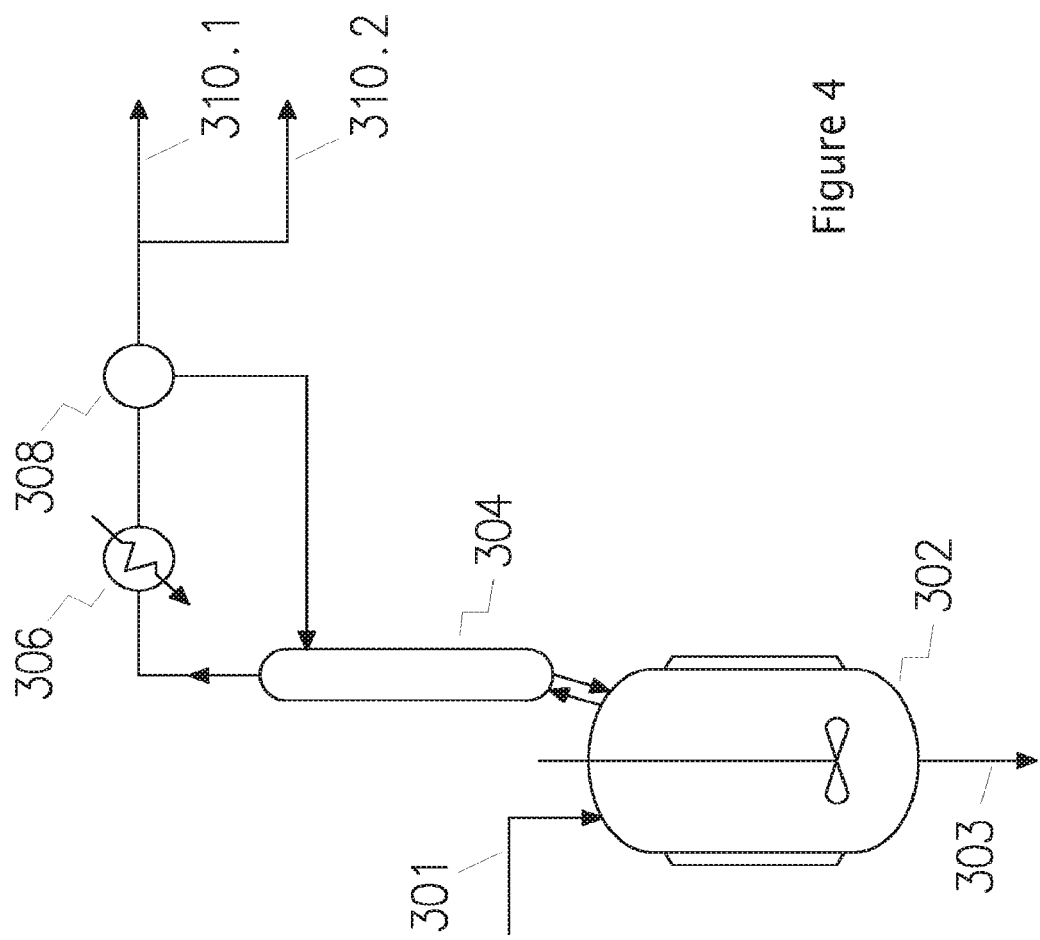

FIG. 4—Second distillation step

| 301 | crude 1,1,1,3-tetrachloropropane product feed stream |
| 302 | distillation boiler |
| 303 | heavy ends residue |
| 304 | distillation column |
| 306 | condenser |
| 308 | reflux divider |
| 310.1 | purified 1,1,1,3-tetrachloropropane product stream |
| 310.2 | chlorinated pentane/pentene stream |

EXAMPLES

The present invention is now further illustrated in the following examples.

Example 1—Demonstration of Catalytic Ability of Recovered Catalyst Using an Aqueous Treatment Ethene and carbon tetrachloride were reacted to produce 1,1,1,3-Tetrachloropropane in the presence of catalyst which was either i) recovered from a reaction mixture using conventional distillation techniques, or ii) recovered from a reaction mixture using the inventive aqueous treatment step for catalyst described herein. The reaction mixture additionally comprised 1,1,1,3-Tetrachloropropane (present in the recycle stream) and tetrachloropentane (a chlorinated alkane impurity commonly formed as a byproduct in the presence of telomerisation reactions between carbon tetrachloride and ethene).

These test examples show that using the aqueous treatment step to recover catalyst, the performance of the catalyst is significantly higher as compared to catalyst recovered using conventional distillation techniques.

For brevity, the following terms are used in the examples set out below:
TeCM: tetrachloromethane.
TeCPa: 1,1,1,3-Tetrachloropropane
TeCPna: tetrachloropentane,
$Bu_3PO_4$: Tributylphosphate Gas chromatography was used to monitor the progress of the reaction.

Batchwise Arrangement

A stainless steel autoclave with a volume of 405 ml, equipped with a stirrer, a thermowell for temperature measurement and a sampling tube (with valve) was filled with the reaction mixture described below and closed. Heating was provided by means of an oil bath placed on a magnetic (heating) stirrer. Ethene was fed by a copper capillary tube from 10 l cylinder placed on weighing scale. The gaseous atmosphere in the autoclave was replaced by ethene flushing. After pressurizing with ethene to 5 bar, the autoclave was heated up to 105° C., then the ethene supply to the autoclave was opened. Ethene supply was controlled manually for a first ten minutes (to maintain the reaction temperature to 112° C.), and later was maintained at a constant pressure of 9 bar. The reaction was allowed to react defined time period. Than the reactor was cooled and reaction mixture was withdrawn after opening of depressurised reactor.

Comparative Examples 1-1 and 1-3 and Examples 1-2, 1-4 and 1-5

In the first example, the distillation residue was directly used as a recycled catalyst (Comparative Example 1-1). In the second example, the distillation residue was extracted with 5% hydrochloric acid and a filtered organic fraction was used as a catalyst (Example 1-2).

Comparative Example 1-1

90.1 g of a distillation residue comprising 63.7% TeCPa, 22.8% TeCPna and 7.49% $Bu_3PO_4$ was mixed with 400 g of TeCM. The mixture was then introduced into the autoclave where 5.0 g of iron was added. After flushing with ethene, the mixture was heated in the autoclave up to 110° C. At this temperature and at a pressure of 9 bar of ethene, the reaction mixture was allowed to react for 4.5 hours. The first sample was taken after 3 hours. The concentration of residual TeCM at the end of the experiment was 19.7% (33.0% after 3 hours).

Example 1-2

90.1 g of a distillation residue comprising 63.7% TeCPa, 22.8% TeCPna and 7.49% $Bu_3PO_4$ was extracted with 370 g of 5% HCl. A bottom organic layer was filtered and mixed with 400 g TeCM. The mixture was then introduced into the autoclave where 5.0 g of iron was added. After flushing with ethene, the mixture was heated in the autoclave up to 110° C. At this temperature and at a pressure of 9 bar of ethene, the reaction mixture was allowed to react for 4.5 hours. The first sample was taken after 3 hours. The concentration of residual TeCM at the end of the experiment was 5.5% (24.6% after 3 hours).

Comparative Example 1-3

Comparative Example 1-3 was carried out using identical conditions as those employed in Comparative Example 1-1, except that differing concentrations of tetrachloromethane and tributylphosphate were used.

Example 1-4 and 1-5

Examples 1-4 and 1-5 were carried out using identical conditions as those employed in Example 1-2, except that differing concentrations of tetrachloromethane and tributylphosphate were used.

The results of Comparative Example 1-1 and Example 1-2, and Comparative Example 1-3 and Examples 1-4 and 1-5 are shown in the following table. As can be seen, the percentage of tetrachloromethane which was converted to 1,1,1,3-Tetrachloropropane is significantly higher in Examples 1-2, 1-4 and 1-5 than in Comparative Examples 1-1 and 1-3 demonstrating that the performance of an aqueous treatment step when recovering the catalyst has a profound positive effect on the system. This is due to the high viability of the catalyst recovered from the distillate residue and also potentially due to the removal of impurities (e.g. oxygenated impurities) from the reaction mixture which otherwise may retard the reaction.

| Example | $Bu_3PO_4$ | % TeCM in the feedstock | % of reacted TeCM 3 hrs. | 4.5 hrs. |
|---|---|---|---|---|
| Comparative Example 1-1 | 1.37% | 84.7% | 57.4% | 73.8% |
| Example 1-2 | 1.35% | 83.7% | 67.3% | 92.4% |
| Comparative Example 1-3 | 1.77% | 78.7% | 60.0% | 78.1% |
| Example 1-4 | 1.64% | 81.2% | 87.7% | 99.4% |
| Example 1-5 | 1.64% | 70.6% | 78.7% | 99.4% |

Continuous Arrangement:

The same stainless steel autoclave as described above for the batch experiments was used as a stirred flow continuous reactor. The reactor was initially filled with approximately 455 g of reaction mixture. After pressurizing with ethene to 5 bar, the autoclave was heated up to 105° C., then the ethene supply to the autoclave was opened, with continuous feed of the raw material and continuous withdrawal of the reaction mixture started.

Feedstock solution with dissolved catalyst was fed into the autoclave from a stainless steel tank. The tank was placed above the reactor, and thus, a pump was not used for feeding the reactor. Reactor and tank were under an atmosphere of ethene distributed by copper capillaries from the cylinder, with conditions in the cylinder selected to prevent commencement of the reaction. Sampling of the reaction mixture was carried out by sampling tube every five minutes. To monitor the course of the reaction, the container with the feedstock and dissolved catalyst, cylinder of ethene and the withdrawn reaction mixture were weighed. The reaction mixture was always collected for an hour and after that, the collecting vessel is replaced.

Comparative Example 1-6 and 1-8 and Examples 1-7 and 1-9

Continuous experiments comparing the activity of recycled catalyst (i.e. a distillation residue were conducted with and without performance of an aqueous treatment step. In the first case, the distillation residue was directly used as a recycled catalyst (Comparative Example 1-6). In the latter cases, the reaction mixture, after aqueous treatment of the distillation residue with 5% HCl, was used as a raw material containing recycled catalyst (Examples 1-4 and 1-5).

Comparative Example 1-6

587.5 g of the distillation residue comprising 63.7% TeCPa, 22.8% TeCPna and 7.49% Bu3PO4 was mixed with 2200 g of TeCM. This mixture comprised 78.7% TeCM, 11.8% TeCPa, 5.8% TeCPna and was used as a feed stream for the continuous arrangement. The reaction vessel constituted an autoclave was filled with reaction mixture and 8 g of fresh iron. The reaction was carried out at 110° C. with a pressure of ethene of 9 bar. The residence time was 2.7 hours. During the reaction, the amount of reacted TeCM ranged between 75-76%.

Example 1-7

587.5 g of the distillation residue comprising 63.7% TeCPa, 22.8% TeCPna 7.49% $Bu_3PO_4$ was added dropwise over 1.5 hour into 1001.5 g of boiling 5% HCl. This mixture was then stripped. From the overhead product, an organic phase was collected and an aqueous phase was returned as a reflux. Distillation was terminated after an hour when all of the distillation residue was added. The residue, after stripping, was diluted with 200 g of TeCM and then separated in a separatory funnel. A bottom organic phase was filtered and together with distilled residue was mixed with 2000 g of TeCM. This mixture comprised 81.2% TeCM, 10.8% TeCPa and 5.3% TeCPna. It was used as a feed stream for the continuous arrangement of the experiment. The reaction vessel (autoclave) was filled with the older reaction mixture and 8 g of fresh iron. The reaction was carried out at 110° C. and a pressure of ethene of 9 bar. Residence time was 2.7 hours/flow rate. During the time of the reaction the amount of reacted TeCM ranged between 83-85%.

Comparative Example 1-8

Comparative Example 1-8 was carried out using identical conditions as those employed in Comparative Example 1-6, except that differing concentrations of tetrachloromethane and tributylphosphate were used.

Example 1-9

Example 1-9 was carried out using identical conditions as those employed in Example 1-7, except that differing concentrations of tetrachloromethane and tributylphosphate were used.

| Example (recycled catalyst) | $Bu_3PO_4$ | % TeCM in the feedstock | % reacted TeCM |
| --- | --- | --- | --- |
| Comparative Example 1-6 | 1.67% | 78.7% | 75.0% |
| Example 1-7 | 1.64% | 81.2% | 84% |
| Comparative Example 1-8 | 1.83% | 76.8% | 60% |
| Example 1-9 | 1.89% | 78.0% | 89% |

Example 2—Preparation of High Purity 1,1,1,3-Tetrachloropropane

High purity 1,1,1,3-Tetrachloropropane may be obtained according to a process of the present invention involving an alkylation step (FIG. 1), a first distillation step (FIG. 2), an aqueous catalyst recovery step (FIG. 3) and a second distillation step (FIG. 4). However, it will be appreciated that not all of these steps are necessary to obtain high purity $C_{3-6}$ alkane according to the processes of the present invention.

In the alkylation step shown in FIG. 1, ethene and particulate iron are fed via lines 1 and 2 into a continuously stirred tank reactor 3. The ethene is introduced into the continuously stirred tank reactor 3 in gaseous form via a dip tube provided with a nozzle. A controlled feed of particulate iron is fed into the continuously stirred tank reactor 3.

Particulate iron is intermittently fed into the continuously stirred tank reactor 3 using a controlled feed. The ongoing addition of particulate iron is employed because, as the alkylation reaction proceeds, particulate iron dissolves into the reaction mixture. It has been found that optimal results are obtained by maintaining the presence of particulate iron in the reaction mixture, in this example with the addition of 1 to 2% by weight of the reaction mixture in the primary alkylation zone. This results in the reaction mixture extracted from the primary alkylation zone having a dissolved iron content of 0.2 to 0.3% by weight of the reaction mixture.

Carbon tetrachloride is fed into the continuously stirred tank reactor 3 via line 12 in liquid form. In the illustrated embodiment, the carbon tetrachloride stream is used to trap gaseous ethene extracted from the reaction mixture. However, the use of carbon tetrachloride in this way is not essential to the present invention; a feed of fresh carbon tetrachloride as the sole or main source of carbon tetrachloride could be fed into the reactor 3.

Tributyl phosphate/ferric chloride catalyst is also fed into the continuously stirred tank reactor 3 via line 12. The tributyl phosphate present in that stream is partly obtained from the aqueous treatment process illustrated in FIG. 3 (and discussed below in more detail), with the balance being provided as fresh tributyl phosphate added into the system. The stream in line 12 additionally comprises a haloalkane extraction agent.

In the illustrated embodiment, a single primary alkylation zone is employed, located in the continuously stirred tank reactor 3. Of course, if required, a plurality of primary alkylation zones could be employed, for example in one or more continuously stirred tank reactors, that could be operated in parallel and/or in series.

The primary alkylation zone is operated under superatmospheric pressure (5 to 8 bar gauge) and elevated temperature (105° C. to 110° C.) and for a residence time of 100-120 minutes. These conditions are selected to cause the carbon tetrachloride and ethene to form 1,1,1,3-Tetrachloropropane in an alkylation reaction. However, it has been found that the total conversion of carbon tetrachloride to 1,1,1,3-Tetrachloropropane is undesirable as this also results in the formation of unwanted impurities. Thus the level of conversion of the carbon tetrachloride to the chlorinated $C_{3-6}$ alkane of interest is controlled and, in this embodiment of the invention, is not permitted to proceed beyond 95% Control of the progress of the alkylation reaction is achieved partly through use of reaction conditions which do not favour the total conversion of carbon tetrachloride to 1,1,1, 3-Tetrachloropropane, through control of the residence time of the reaction mixture in the continuously stirred tank reactor.

Reaction mixture comprising i) unreacted carbon tetrachloride and ethene, ii) 1,1,1,3-Tetrachloropropane (the chlorinated $C_{3-6}$ alkane of interest in this embodiment) and iii) tributyl phosphate/iron chloride catalyst is extracted from the primary alkylation zone (the continuously stirred tank reactor 3) and fed into a plug/flow reactor 4 (in which the principal alkylation zone is located).

The reaction mixture is extracted such that particulate iron catalyst present in the primary alkylation zone 3 is not extracted and thus the reaction mixture is substantially free of particulate material. Further, in the illustrated embodiment, no additional catalyst is added into the plug/flow reactor 4, although the plug/flow reactor 4 may provided with a catalyst bed. Additionally, no further ethene is added into the plug/flow reactor 4.

In the illustrated embodiment, the operating pressure in the principal alkylation zone 4 is the same as that in the primary alkylation zone 3. The residence time of the reaction mixture is about 30 minutes, which in the illustrated embodiment was sufficient to result in substantially all of the ethene present being used up in the reaction. Of course, it will be understood that for different reactor types and operating conditions, different resident times may be optimal.

When the determined optimal residence time of the reaction mixture in the principal alkylation zone has been reached, reaction mixture is extracted therefrom via line 5, while being maintained at elevated pressure and temperature, and fed into flash evaporation vessel 6. In this vessel, the extracted reaction mixture is subjected to depressurisation, to atmospheric pressure. This pressure drop causes evaporation of the ethene present in the reaction mixture. The 1,1,1,3-Tetrachloropropane-rich mixture, now with substantially no ethene present, is extracted from the flash vessel via line 7 and subjected to the distillation step shown in FIG. 2, and discussed below in more detail.

The evaporated ethene is extracted from the flash vessel 6 via line 8 and fed through a condenser 9. The ethene is then fed via line 10 into absorption column 11 where it is contacted with a stream of carbon tetrachloride and tributyl phosphate/iron chloride catalyst, recovered from the reaction mixture in the aqueous treatment step shown in FIG. 3, and discussed below in more detail. The stream of recovered catalyst/carbon tetrachloride 13 is passed through a cooler 14 and then fed via line 15 into the absorption column 11.

The flow of cooled carbon tetrachloride/catalyst through the absorption column 11 has the effect of trapping the ethene therein. The obtained liquid flow of carbon tetrachloride/catalyst/ethene is then fed back into the continuously stirred tank reactor 3.

As is apparent from FIG. 1, the illustrated embodiment includes an ethene recycling loop which is advantageous for several reasons. First, almost total utilisation of the ethene is achieved and thus the amount of ethene lost from the system is very low. Additionally, the energy requirements of the components of the ethene recycling system are also low. Further, the amount of ethene lost from the system is also very low, meaning that the environmental burden is reduced.

Turning now to FIG. 2, the 1,1,1,3-Tetrachloropropane-rich mixture extracted from the flash vessel shown with reference numeral 6 in FIG. 1, is fed via line 101 into a batch distillation boiler 102 which is operated in communication with a vacuum distillation column 104. The distillation boiler is operated at a temperature of 90° C. to 95° C. Chloroalkanes present in the mixture fed into the boiler 102 are evaporated and separated using distillation column 104 (and the downstream condenser 106 and reflux divider 108) into light ends stream 110.1, carbon tetrachloride stream 110.2, tetrachloroethene stream 110.3 and purified 1,1,1,3-Tetrachloropropane product stream 110.4.

The light ends and tetrachloroethene streams 110.1, 110.3 may be used in the production of carbon tetrachloride, advantageously minimising the production of waste products. This can be achieved through use of a high temperature chlorinolysis process.

The carbon tetrachloride stream 110.2 is recycled back into the continuously stirred tank reactor 103. The purified 1,1,1,3-Tetrachloropropane product stream 110.4 is extracted from the system and may be stored for shipment or employed in downstream processes requiring pure 1,1,1,3-Tetrachloropropane as a starting material.

A 1,1,1,3-Tetrachloropropane-rich mixture which also comprises catalyst is extracted as a residue from boiler 102 via line 103 and is subjected to the catalyst recovery step shown in FIG. 3.

In that step, the 1,1,1,3-Tetrachloropropane-rich mixture is fed into a batch distillation boiler 204 via line 202, along with a weak (1-5%) hydrochloric acid solution via line 201.

Advantageously, the water present in the acid solution deactivates the catalyst system and protects it from thermal damage. This enables the catalyst system, to be recovered from the 1,1,1,3-Tetrachloropropane-rich mixture, and it can be easily reactivated, post-recovery, and reused in the alkylation process without any significant loss in catalytic activity.

The batch distillation boiler is operated at a temperature of about 100° C., to create a gaseous mixture comprising 1,1,1,3-Tetrachloropropane and water vapour.

The gaseous mixture produced in the boiler 204, is then subjected to steam distillation (or steam stripping) of crude 1,1,1,3-Tetrachloropropane in column 210, which is coupled to the boiler 204. The crude 1,1,1,3-Tetrachloropropane is extracted from the distillation column 210 via line 211, condensed with a condenser 212, fed via line 213 to a reflux liquid-liquid separator 214. Water from the gaseous mixture is fed back to the distillation column 210 via line 215, and a portion is taken off via line 216 for a further distillation step, shown in more detail in FIG. 4 and discussed below in more detail.

The operating temperature of the boiler 204 is then reduced to stop steam stripping, resulting in the condensation of the water vapour present therein. This results in the formation of a biphasic mixture containing an aqueous phase and an organic phase containing the catalyst system, which has not be subjected to steam stripping. To facilitate extraction of the organic phase, a haloalkane extraction agent (in this case, 1,1,1,3-Tetrachloropropane) is added to the boiler 204 via line 203 to increase the volume of that phase.

Extraction of the organic phase from the biphasic mixture is achieved by the sequential extraction of the phases from the boiler 204 via line 205. The organic phase is extracted from the boiler 204 via line 205 and is filtered 206. A filter cake is removed from the filter 206 via line 207. The organic phase is extracted via line 208 and, in this embodiment, fed back to the primary alkylation zone, as shown in FIG. 1, specifically via line 13 in FIG. 1. The aqueous phase is extracted via line 5, filtered 6 and disposed of via line 209.

The stripped crude 1,1,1,3-Tetrachloropropane product is subjected to a further distillation step shown in FIG. 4. In that step, the crude product is fed into a distillation boiler 302 via line 301. The boiler 302 is in communication with distillation column 304. Evaporated chlorinated organic compounds present in the crude 1,1,1,3-Tetrachloropropane are separated in the distillation column 304 (and related downstream apparatus, condenser 306 and reflux divider 308) into a purified 1,1,1,3-Tetrachloropropane product stream 310.1 and chlorinated pentane/pentene stream 310.2.

The chlorinated pentane/pentene stream 310.2 may be used in the production of carbon tetrachloride, advantageously minimising the production of waste products. This can be achieved through use of a high temperature chlorinolysis process.

The purified 1,1,1,3-Tetrachloropropane product stream 310.1 is extracted from the system and may be combined with the major product stream (identified with reference numeral 110.4 in FIG. 2. The product may be stored for shipment or employed in downstream processes requiring pure 1,1,1,3-Tetrachloropropane as a starting material.

The heavy ends residue extracted from the boiler 302 via line 303 is either disposed of or further processed.

Using the apparatus and process conditions outlined above, 2635 kg of carbon tetrachloride (CTC, 99.97% purity) was continuously processed with an average hourly loading 78.2 kg/h to produce 1,1,1,3-Tetrachlorpropene (1113TeCPa). Basic parameters of disclosed process carried out according to Example 2 are as following.

| Basic parameters | |
|---|---|
| First reactor mean residence time (min) | 118 |
| First reactor temperature range (° C.) | 100-110 |
| First reactor pressure (kPa) | 800 |
| Second reactor mean residence time (min) | 25 |
| Second reactor temperature range (° C.) | 100-110 |
| Second reactor pressure (kPa) | 800 |
| Overall reaction CTC conversion (%) | 91.0 |
| Overall 1113TeCpa reaction yield (mol TeCPa/mol CTC converted, in %) | 95.5 |
| Overall 1113TeCpa yield including the all process steps described in Example 2 | 94.0 |

The full impurity profile of the purified product of the above-described embodiment is presented in the following table. Please note that the figures are given as a weighted average of the profiles for the product obtained in line 110.4 in FIG. 2 and line 310.1 in FIG. 4.

| Compound | (% wt) |
|---|---|
| Trichloromethane | 0 |
| 1,2-Dichloroethane | 0 |
| 1-chlorobutane | 0.023 |
| Tetrachloromethane | 0.008 |
| 1,1,1-Trichloropropane | 0.001 |
| Tetrachloroethene | 0.006 |
| 1,1,3-Trichlroroprop-1-ene | 0.014 |
| 1,1,1,3-Tetrachloropropane | 99.925 |
| 1,1,1,3,3-Pentachloropropane | 0.004 |
| hexachloroethane | 0.012 |
| 1,1,1,2,3-Pentachloropropane | 0.005 |
| 1,1,1,5-Tetrachloropentane | 0 |
| 1,3,3,5-Tetrachloropentane | 0 |
| Tributylphosphate | 0 |
| Unknown | 0.007 |

Example 3: Effect on Selectivity of Molar Ratio of Starting Material:Product in Reaction Mixture These examples were carried out using the equipment and techniques outlined above in the 'Continuous Arrangement' in Example 1, except where otherwise stated. The molar ratio of the chlorinated $C_{3-6}$ alkane product (in this case, 1,1,1,3-Tetrachloropropane):carbon tetrachloride in the reaction mixture was controlled to differing levels, principally by the residence time of reaction mixture in the alkylation zone. Temperature was maintained at 110° C. and pressure was maintained at 9 Bar. The selectivities towards product of interest are reported in the following table:

| Trial No. | mol. ratio 1113TeCPa:Tetrachloromethane | Selectivity of Tetrachloromethane towards 1113TeCPa |
|---|---|---|
| 3-1 | 79.0:21.0 | 96.6 |
| 3-2 | 84.4:15.6 | 95.2 |
| 3-3 | 89.8:10.2 | 95.5 |
| 3-4 | 93.9:6.1 | 94.1 |
| 3-5 | 98.0:2.0 | 90.3 |

As can be seen from this example, when the molar ratio of product:starting material exceeds 95:5 when the process is operated on a continuous basis, there is a notable reduction in selectivity towards the product of interest.

Example 4: Effect on Selectivity of Molar Ratio of Starting Material:Product in Reaction Mixture These examples were carried out using the equipment and techniques as illustrated in FIG. 1, with reference to the accompanying text in Example 2 above, except where otherwise stated. The molar ratio of the chlorinated $C_{3-6}$ alkane product (in this case, 1,1,1,3-Tetrachloropropane): carbon tetrachloride in the reaction mixture was controlled to differing levels, principally by control of the feed rate of the ethylene starting material. Temperature was constantly 110° C. The selectivities towards the product of interest are reported in the following table:

| Trial No. | mol. ratio 1113TeCPa:Tetrachloromethane | Selectivity of Tetrachloromethane towards 1113TeCPa |
|---|---|---|
| 4-1 | 91.5:8.5 | 95.6 |
| 4-2 | 95.3:4.7 | 94.8 |
| 4-3 | 96.4:3.6 | 93.3 |
| 4-4 | 97.0:3.0 | 92.9 |

As can be seen from this example, when the molar ratio of product:starting material exceeds 95:5 when the process is operated on a continuous basis, there is a notable reduction in selectivity towards the product of interest.

Example 5: Effects of Feedstock Purity

These examples were carried out using the equipment and techniques as illustrated in FIG. 2, with reference to the accompanying text in Example 2 above, except where otherwise stated. Trial 5-1 is the stream obtained from stream 110.4 in FIG. 2. Trials 5-2-5-5 are alternative examples, obtained using the same apparatus and techniques, but employing feedstocks of differing purity. The data below demonstrates that although lower purity feedstock was used in trials 5-2 to 5-5, this advantageously does not significantly impact product purity when obtained from processes of the present invention.

| | Trial No. | | | | |
|---|---|---|---|---|---|
| Compounds | 5-1 | 5-2 | 5-3 | 5-4 | 5-5 |
| 1-chlorobutane | 0.004 | 0.028 | 0.032 | 0.011 | 0.002 |
| TeCM | 0.0004 | 0.007 | 0.004 | 0.014 | 0.006 |
| 1,1,1-trichloropropane | 0 | 0 | 0.0005 | 0.004 | 0.009 |
| Tetrachloroethene | 0.002 | 0.001 | 0.002 | 0.02 | 0.052 |
| 1,1,3-trichloropropene | 0.01 | 0.025 | 0.017 | 0.013 | 0.065 |
| 1,1,1,3-tetrachloropropane | 99.96 | 99.81 | 99.92 | 99.89 | 99.836 |

-continued

| Compounds | Trial No. | | | | |
|---|---|---|---|---|---|
| | 5-1 | 5-2 | 5-3 | 5-4 | 5-5 |
| 1,1,1,3,3-pentachloropropane | 0.0002 | 0.017 | ND | ND | ND |
| Hexachlorethane | 0.002 | 0.079 | 0.002 | 0.013 | 0.001 |
| 1,1,1,2,3-pentachloropropane | 0.0004 | 0.003 | 0 | 0.004 | ND |
| Others | 0.023 | 0.033 | 0.022 | 0.031 | 0.028 |

Example 6: CSTR and Plug Flow Combination

These examples were carried out using the equipment and techniques as illustrated in FIG. 1, with reference to the accompanying text in Example 2 above, except where otherwise stated. The efficiency of reaction in the second plug-flow reactor (reference numeral 4 in FIG. 1) was evaluated. Two trials were conducted with differing amount of dissolved ethylene at the inlet of the plug-flow reactor which was operated at the same temperature, 110° C., as the main CSTR reactor (reference numeral 3 in FIG. 1). The results are shown in the following table:

| Trial No. | Ethylene content at plug-flow reactor inlet (%) | TeCM content at plug-flow reactor intlet (%) | Ethylene content at plug-flow reactor outlet (%) | TeCM content at plug-flow reactor outlet (%) |
|---|---|---|---|---|
| 6-1 | 1.19 | 12.5 | 0.087 | 6.58 |
| 6-2 | 0.36 | 9.17 | 0.089 | 6.99 |

As can be seen from this example, there is a conversion of ethylene between 75-93% in the plug-flow reactor. Thus if plug-flow reactor is employed there is more efficient ethylene utilization in the reaction section. The serial plug-flow reactor allows the CSTR reactor to be operated at an optimal pressure, without needing complex and uneconomical ethylene recovery processes. The serial plug reactor therefore controls the ethylene use in an efficient closed loop.

Example 7: Problematic Degradation of Catalyst Ligand During Conventional Distillation Fractional distillation equipment consisting of a 2-litre glass distillation four-neck flask equipped with condenser, thermometer, heating bath and vacuum pump system was set up. The distillation flask was initially filled with 1976 grams of reaction mixture obtained using the apparatus and techniques illustrated in FIG. 1 and explained in the accompanying text in Example 2 above.

During distillation, pressure was gradually reduced from an initial pressure of 100 mmHg to a final pressure of 6 mmHg. During this period, 1792 grams of distillate (in different fractions) were extracted. During distillation, there was visible HCl gas formation and furthermore chlorobutane (the breakdown product from tributylphosphate ligand) was also formed in significant amounts namely between 1 to 19% for the distillate fractions. Upon these observations being made, the distillation was interrupted, distillation residue was weighed and analyzed and was found to have a Tetrachloropropane content of 16%. It was no longer possible to continue distillation without significant degradation of the Tributylphosphate ligand.

The invention claimed is:

1. A process for producing a chlorinated $C_{3-6}$ alkane comprising providing a reaction mixture comprising an alkene, carbon tetrachloride and a catalyst in an alkylation zone to produce chlorinated $C_{3-6}$ alkane in the reaction mixture, and extracting a portion of the reaction mixture from the alkylation zone, wherein:
   the concentration of the chlorinated $C_{3-6}$ alkane in the reaction mixture in the alkylation zone is maintained at a level such that the molar ratio of chlorinated $C_{3-6}$ alkane:carbon tetrachloride in the reaction mixture extracted from the alkylation zone does not exceed 95:5 when the alkylation zone is in continuous operation;
   wherein the reaction mixture extracted from the alkylation zone is subjected to an aqueous treatment step with diluted hydrochloric acid in which a biphasic mixture is formed and an organic phase comprising the catalyst is extracted from the biphasic mixture.

2. The process of claim 1, wherein the alkene is ethene, propene and/or chlorinated propene.

3. The process of claim 1, wherein the chlorinated $C_{3-6}$ alkane is 1,1,1,3-tetrachloropropane.

4. The process of claim 1, wherein the catalyst is a metallic catalyst, further comprising an organic ligand.

5. The process of claim 4, wherein the organic ligand is tributylphosphate.

6. The process of claim 1, wherein the organic phase extracted from the biphasic mixture is fed back to the alkylation zone.

7. A process for producing 1,1,1,3-tetrachloropropane, comprising providing a reaction mixture comprising ethene, carbon tetrachloride, a metallic catalyst and an organic ligand in an alkylation zone to produce 1,1,1,3-tetrachloropropane in the reaction mixture, and extracting a portion of the reaction mixture from the alkylation zone, wherein
   the reaction mixture extracted from the alkylation zone is subjected to an aqueous treatment step with diluted hydrochloric acid, in which a biphasic mixture is formed and an organic phase is extracted from the biphasic mixture; and
   the organic phase extracted from the biphasic mixture comprises carbon tetrachloride, 1,1,1,3-tetrachloropropane, tetrachloropentane and the organic ligand.

* * * * *